(12) United States Patent
Receveur

(10) Patent No.: US 9,295,600 B2
(45) Date of Patent: Mar. 29, 2016

(54) PERSON SUPPORT APPARATUS WITH ACTIVITY AND MOBILITY SENSING

(75) Inventor: Timothy J. Receveur, Guilford, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 422 days.

(21) Appl. No.: 13/443,131

(22) Filed: Apr. 10, 2012

(65) Prior Publication Data

US 2012/0259248 A1 Oct. 11, 2012

Related U.S. Application Data

(63) Continuation-in-part of application No. 13/083,140, filed on Apr. 8, 2011, now abandoned.

(30) Foreign Application Priority Data

Apr. 3, 2012 (EP) .................................... 12163052

(51) Int. Cl.
*A61B 5/11* (2006.01)
*A47C 27/08* (2006.01)
(Continued)

(52) U.S. Cl.
CPC .......... *A61G 7/05769* (2013.01); *A61B 5/1118* (2013.01); *G06F 19/3406* (2013.01); *G06F 19/3431* (2013.01); *A61B 5/1115* (2013.01); *A61B 5/447* (2013.01); *A61B 5/6891* (2013.01); *A61B 5/6892* (2013.01); *A61B 5/7435* (2013.01); *A61G 7/005* (2013.01); *A61G 7/012* (2013.01); *A61G 7/015* (2013.01); *A61G 7/018* (2013.01); *A61G 2007/0509* (2013.01);
(Continued)

(58) Field of Classification Search
CPC ... A61G 7/05769; A61G 7/005; A61G 7/012; A61G 7/015; A61G 7/018; A61G 2007/0509; A61G 2007/0514; A61G 2007/0524; A61G 2007/05792; A61G 2203/20; A61G 2203/30; A61G 2203/34; G06F 19/3406; G06F 19/3431; G06F 19/3418; A61B 5/1118; A61B 5/1115; A61B 5/447; A61B 5/6892; A61B 5/7435; A61B 5/6891
USPC .............. 5/600, 613, 616–617, 940; 128/845; 340/562, 573.4, 686.1; 600/484, 595
See application file for complete search history.

(56) References Cited

U.S. PATENT DOCUMENTS

| | | |
|---|---|---|
| 5,647,079 A | 7/1997 | Hakamiun et al. |
| 5,715,548 A | 2/1998 | Weismiller et al. |

(Continued)

OTHER PUBLICATIONS

"Actiwatch," Philips Respironics, 1 page (accessed at www.actiwatch.respironics.com on Nov. 4, 2010).

(Continued)

*Primary Examiner* — Rene Towa
(74) *Attorney, Agent, or Firm* — Barnes & Thornburg LLP

(57) ABSTRACT

A person support apparatus may, among other things, support a person in a laying-down or a seated position. One or more sensors, which may be operably coupled to the person support apparatus, monitor changes in the position of a person situated on the person support apparatus. A control system receives output from the sensor or sensors over a period of time, while the person is positioned on the person support apparatus. The control system makes a determination relating to the activity and/or mobility of the person positioned on the person support apparatus. The control system may use the activity and/or mobility determination to control a feature of the person support apparatus, or for other purposes.

26 Claims, 9 Drawing Sheets

(51) Int. Cl.
*A61G 7/00* (2006.01)
*A61G 7/002* (2006.01)
*A61G 7/057* (2006.01)
*G06F 19/00* (2011.01)
*A61B 5/00* (2006.01)
*A61G 7/005* (2006.01)
*A61G 7/012* (2006.01)
*A61G 7/015* (2006.01)
*A61G 7/018* (2006.01)
*A61G 7/05* (2006.01)

(52) U.S. Cl.
CPC ............... *A61G 2007/0514* (2013.01); *A61G 2007/0524* (2013.01); *A61G 2007/05792* (2013.01); *A61G 2203/20* (2013.01); *A61G 2203/30* (2013.01); *A61G 2203/34* (2013.01); *G06F 19/3418* (2013.01)

(56) References Cited

U.S. PATENT DOCUMENTS

| | | | |
|---|---|---|---|
| 5,794,288 A | 8/1998 | Soltani et al. | |
| 6,021,533 A | 2/2000 | Ellis et al. | |
| 6,067,019 A | 5/2000 | Scott | |
| 6,133,837 A | 10/2000 | Riley | |
| 6,178,578 B1 | 1/2001 | Soltani et al. | |
| 6,185,767 B1 | 2/2001 | Brooke et al. | |
| 6,208,250 B1 | 3/2001 | Dixon et al. | |
| 6,336,235 B1 | 1/2002 | Ruehl | |
| 6,362,725 B1 | 3/2002 | Ulrich et al. | |
| 6,468,234 B1* | 10/2002 | Van der Loos et al. | 600/595 |
| 6,505,368 B1 | 1/2003 | Ellis et al. | |
| 6,691,346 B2 | 2/2004 | Osborne et al. | |
| 6,694,549 B2 | 2/2004 | Perez et al. | |
| 6,708,358 B2 | 3/2004 | Hensley | |
| 6,721,980 B1 | 4/2004 | Price et al. | |
| 6,791,460 B2 | 9/2004 | Dixon et al. | |
| 6,819,254 B2 | 11/2004 | Riley | |
| 6,897,780 B2 | 5/2005 | Ulrich et al. | |
| 6,978,500 B2 | 12/2005 | Osborne et al. | |
| 7,171,708 B2 | 2/2007 | Osborne et al. | |
| 7,242,308 B2 | 7/2007 | Ulrich et al. | |
| 7,253,366 B2 | 8/2007 | Bhai | |
| 7,260,860 B2 | 8/2007 | Chambers et al. | |
| 7,315,535 B2 | 1/2008 | Schuman | |
| 7,325,265 B2 | 2/2008 | Hornbach et al. | |
| 7,330,127 B2 | 2/2008 | Price et al. | |
| 7,396,331 B2 | 7/2008 | Mack et al. | |
| 7,437,787 B2 | 10/2008 | Bhai | |
| 7,454,805 B2 | 11/2008 | Osborne et al. | |
| 7,458,119 B2 | 12/2008 | Hornbach et al. | |
| 7,464,605 B2 | 12/2008 | Douglas et al. | |
| 7,469,436 B2 | 12/2008 | Meyer et al. | |
| 7,487,562 B2 | 2/2009 | Frondorf et al. | |
| 7,500,280 B2 | 3/2009 | Dixon et al. | |
| 7,515,059 B2 | 4/2009 | Price et al. | |
| 7,523,515 B2 | 4/2009 | Allen et al. | |
| 7,538,659 B2 | 5/2009 | Ulrich et al. | |
| 7,540,841 B2 | 6/2009 | Azzaro et al. | |
| 7,557,718 B2 | 7/2009 | Petrosenko et al. | |
| 7,568,246 B2 | 8/2009 | Weismiller et al. | |
| 7,610,637 B2 | 11/2009 | Menkedick et al. | |
| 7,610,638 B2 | 11/2009 | Kramer et al. | |
| 7,617,555 B2 | 11/2009 | Romano et al. | |
| 7,746,218 B2 | 6/2010 | Collins, Jr. et al. | |
| 7,784,128 B2 | 8/2010 | Kramer | |
| 7,849,945 B2 | 12/2010 | Ross, VII et al. | |
| 7,883,478 B2 | 2/2011 | Skinner et al. | |
| 2004/0087878 A1* | 5/2004 | Krausman et al. | 600/587 |
| 2005/0081300 A1 | 4/2005 | O'Reagan et al. | |
| 2005/0273940 A1* | 12/2005 | Petrosenko et al. | 5/722 |
| 2006/0028350 A1* | 2/2006 | Bhai | 340/666 |
| 2007/0266499 A1 | 11/2007 | O'Keefe et al. | |
| 2008/0189865 A1 | 8/2008 | Bhai | |
| 2008/0275349 A1* | 11/2008 | Halperin et al. | 600/484 |
| 2009/0203972 A1 | 8/2009 | Heneghan et al. | |
| 2010/0152543 A1 | 6/2010 | Heneghan et al. | |
| 2010/0302044 A1* | 12/2010 | Chacon et al. | 340/575 |
| 2011/0024076 A1 | 2/2011 | Lachenbruch et al. | |
| 2011/0068939 A1* | 3/2011 | Lachenbruch | 340/626 |
| 2011/0263950 A1* | 10/2011 | Larson et al. | 600/301 |
| 2013/0006151 A1* | 1/2013 | Main et al. | 600/587 |

OTHER PUBLICATIONS

"Actigraphy," Wikipedia, the free encyclopedia, 3 pages (accessed at http://en.wikipedia.org/wiki/Actigraphy on Nov. 4, 2010).
"Twice as easy," Philips Respironics, 2009, 4 pages.
"Actiwatch Bibliography," Philips Respironics, 2010, 18 pages.
"A trio of solutions," Philips Respironics, 2009, 4 pages.
Barbara Braden and Nancy Bergstrom, "Braden Scale for Predicting Pressure Sore Risk," 1988, 1 page (accessed at www.bradenscale.com on Jul. 4, 2012).

* cited by examiner

PERSON SUPPORT APPARATUS WITH ACTIVITY AND MOBILITY SENSING

CROSS-REFERENCE TO RELATED APPLICATIONS

This application is a continuation-in-part of and claims priority to U.S. patent application Ser. No. 13/083,140, filed Apr. 8, 2011, and claims priority to European Patent Application No. EP 12163052.9, filed Apr. 3, 2012, both of which are incorporated herein by this reference in their entirety.

BACKGROUND

This disclosure relates generally to person support apparatuses that are capable of supporting a person in one or more positions, including a laying-down position or a seated position. Such person support apparatuses include mattresses, cushions, beds, stretchers, chairs, wheelchairs, tables, and other similar devices. Person support apparatuses of this type may be found, for example, in healthcare facilities, homes, and other locations in which care is provided.

More particularly, this disclosure relates to systems in which changes in the position of a person located on a person support apparatus, relative to the person support apparatus, are monitored. Currently, monitoring systems exist that detect relatively large-scale movements, or the lack thereof, of a person relative to a person support apparatus. Such movements typically include changes in position that indicate that the person has exited, is in the process of exiting, or is preparing to exit the person support apparatus, and/or movements away from the center of the person support apparatus. Some examples are disclosed in U.S. Pat. Nos. 6,362,725; 6,721,980; 6,819,254; 6,791,460, 6,897,780; 7,242,308; 7,253,366; 7,315,535; 7,330,127; 7,538,659; 7,557,718; 7,568,246; and 7,746,218. Often, the purpose of these systems is to alert a caregiver when a person is moving or has moved to a position in which the person is at risk of an adverse event occurring, such as a position near the edge of the person support apparatus.

In some cases, these and other systems adjust mattress pressures in real time, in response to relatively large-scale changes in the person's position on the person support apparatus (e.g. movement from a laying down position to a sitting up position). Some examples are disclosed in U.S. Pat. Nos. 5,794,288; 6,178,578; 7,437,787; 7,500,280; 7,849,945; 7,883,478; and U.S. Patent Application Pub. No. 2008/0189865. Often, the purpose of these systems is to increase the person's comfort or reduce the risk of pressure sores.

Further, some existing systems monitor the physiological activity of a person (e.g. heart rate, breathing rate) while the person is positioned on a person support apparatus. These systems are able to detect very slight movements (such as a heartbeat or the rise and fall of a person's chest). Some examples are disclosed in U.S. Pat. Nos. 6,721,980; 7,330,127; and 7,515,059. These systems are often used to detect the onset of adverse events related to a person's health.

It is believed that few, if any, systems exist that are directed to assessing the activity and/or mobility of a person, while the person is situated on a person support apparatus, and using the activity and/or mobility assessment to configure a person support apparatus in accordance with this disclosure.

SUMMARY

The present invention comprises one or more of the features recited in the appended claims and/or the following features which, alone or in any combination, may comprise patentable subject matter.

According to one aspect of this disclosure, a person support system includes a person support apparatus configured to support a person in one or more positions, and one or more sensors coupled to the person support apparatus. The sensor or sensors are responsive to changes in the position of a person relative to the person support apparatus while the person is supported by the person support apparatus. The person support system also includes a control system, which is operably coupled to the sensor and the person support apparatus, and configured to: receive a plurality of outputs from the at least one sensor over a period of time, make an assessment relating to the person's activity and/or mobility, based on the outputs, where the assessment relating to the person's activity and/or mobility is indicated by changes in position of the person's body or an extremity thereof, relative to the person support apparatus, which are greater in degree than movement that indicates physiological activity of the person and less than or equal in degree to changes in position that indicate a major change in the person's position, determine a person type of the person being supported by the person support apparatus based on the activity and/or mobility assessment, and enable, disable, or configure an electronically-controllable feature of the person support apparatus based on the person type.

The person support apparatus may be a mattress, cushion, bed, stretcher, chair, table, or similar apparatus. The sensor may be a load cell, inclinometer, accelerometer, pressure sensor, force sensor, optical sensor, or the like. The control system may be included in an on-board control system of the person support apparatus. The control system may derive an activity and/or mobility score from the outputs, and the activity and/or mobility score may comprise a value or values corresponding to the person's assessed activity and/or mobility.

The control system may set a time period during which the outputs of the at least one sensor are monitored and perform a mathematical computation (e.g. a standard deviation) using data represented by the outputs received during the time period. The control system may compare the calculated value or values to a threshold value. The control system may be configured to display an indication of the person's activity and/or mobility at a display that is coupled to the person support apparatus. The control system may communicate an indication of the person's activity and/or mobility to a remote device.

The control system may determine a "person type" (e.g. mobile or immobile, bedridden, chairbound, or ambulatory), enable an electronically controllable feature of the person support apparatus if the person type is a first person type, or disable an electronically controllable feature of the person support apparatus if the person type is a second person type different than the first person type. The control system may select a person type from a plurality of person types based on the person's activity and/or mobility assessment. The control system may configure a user control based on the person type.

The control system may use a first plurality of the plurality of the outputs to calibrate the mobility assessment. The control system may permit a user to override the enabling, disabling, or configuring of an electronically-controllable feature of the person support apparatus. The enabling, disabling, or configuring of an electronically-controllable feature of the person support apparatus based on the person type may include enabling a user to enable, disable, or configure an electronically-controllable feature of the person support apparatus based on the person type.

According to another aspect of this disclosure, a control system for a person support apparatus includes one or more sensors coupled to the person support apparatus, where the sensor or sensors are responsive to changes in the position of a person while the person is supported by the person support apparatus. The control system also includes a processor operably coupled to the at least one sensor and the person support apparatus. The processor is configured to: receive a plurality of first outputs from the at least one sensor, the plurality of first outputs being indicative of the person's position relative to the person support apparatus while the person is supported by the person support apparatus, make an assessment relating to the person's activity and/or mobility, based on the first outputs, where the assessment of the person's activity and/or mobility is based on changes in position of the person's body or an extremity thereof, which are greater in degree than movement that indicates physiological activity of the person and less than or equal in degree to changes in position that indicate a major change in the person's position, determine a person type of the person being supported by the person support apparatus based on the activity and/or mobility assessment, and enable, disable, or configure an electronically-controllable feature of the person support apparatus based on the person type.

The processor may receive a plurality of second outputs from the at least one sensor, wherein the plurality of second outputs are indicative of the person's position relative to the person support apparatus, and may make an assessment relating to the person's degree of physical activity and/or mobility, based on the second outputs. The assessment of the person's degree of physical activity is based on changes in the position of the person's body or an extremity thereof, which are greater than changes in position that indicate the person's mobility. The assessment of the person's degree of physical activity may be indicative of the person's ability to ingress or egress the person support apparatus without assistance from another person.

The processor may determine a person type based on the mobility assessment and/or the activity assessment, where the person type indicates whether the person is mobile or immobile, bedridden, chairbound, or ambulatory, for example. The person support apparatus may include an air bladder and the processor may enable, disable, or configure an air pressure adjustment or an airflow feature of the person support apparatus based on the person type.

The person support apparatus may include a low airloss feature and the processor may enable, disable, or configure the low airloss feature based on the person type. The person support apparatus may include an articulating deck and the processor may enable, disable, or configure a feature of the articulating deck based on the person type. The person support apparatus may include a plurality of therapy features and the processor may enable, disable, or configure a therapy feature of the person support apparatus based on the person type.

According to a further aspect of this disclosure, a method of determining a person's activity and/or mobility while the person is situated on a person support apparatus includes sensing changes in the position of a person relative to the person support apparatus while the person is supported by the person support apparatus for a period of time, identifying changes in position of the person's body or an extremity thereof, during the period of time, which are greater in degree than movement that indicates physiological activity of the person and less than or equal in degree than changes in position that indicate a major change in the person's position, making an assessment of the person's activity and/or mobility based on the identified changes, and outputting an indication of the person's activity and/or mobility based on the activity and/or mobility assessment.

BRIEF DESCRIPTION OF THE DRAWINGS

The detailed description particularly refers to the following figures, in which.

DETAILED DESCRIPTION

Figure 1:
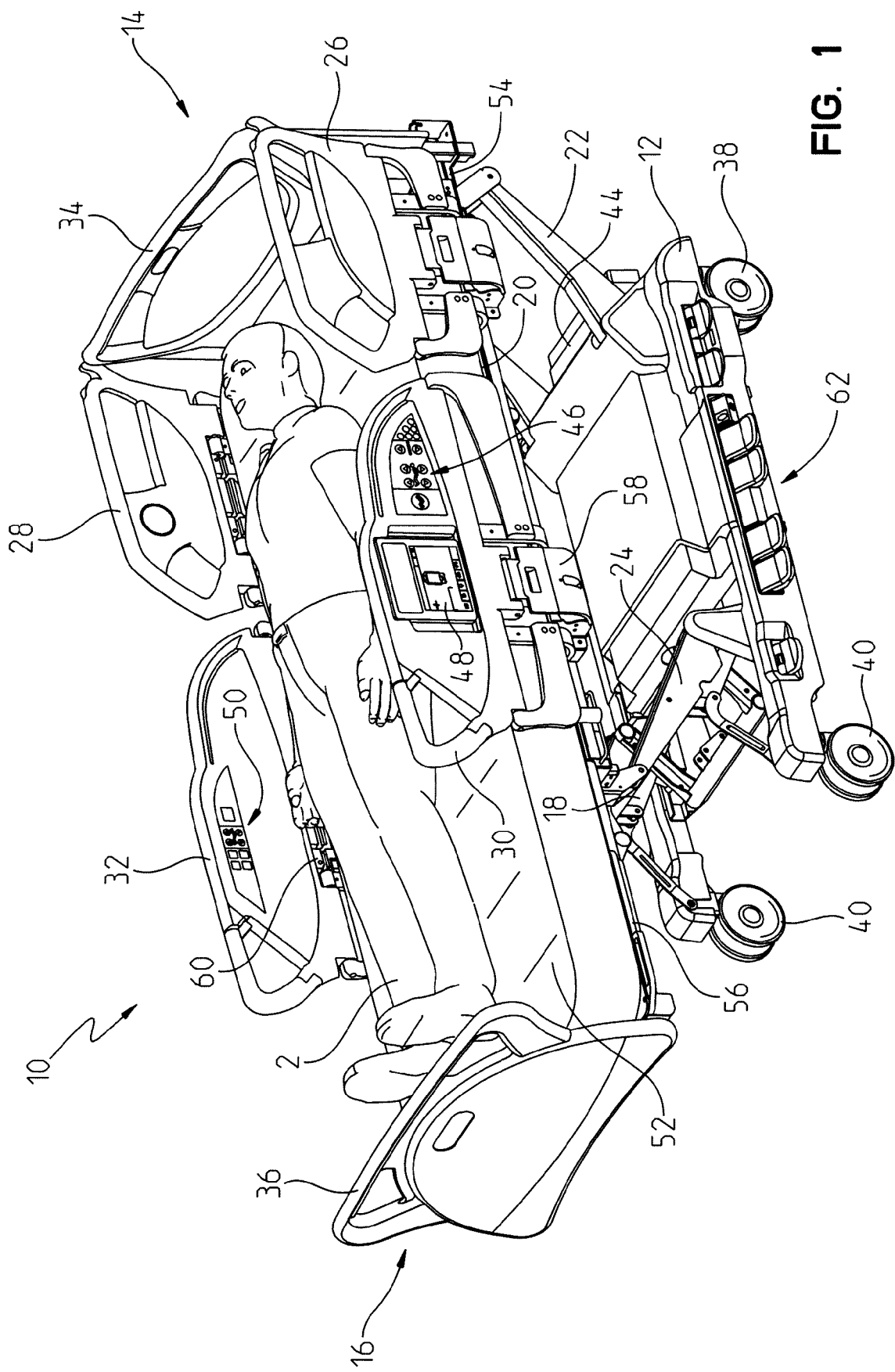
FIG. 1 is a simplified perspective view of at least one embodiment of a person support apparatus having activity and/or mobility sensing features in accordance with this disclosure.
Figure 2:
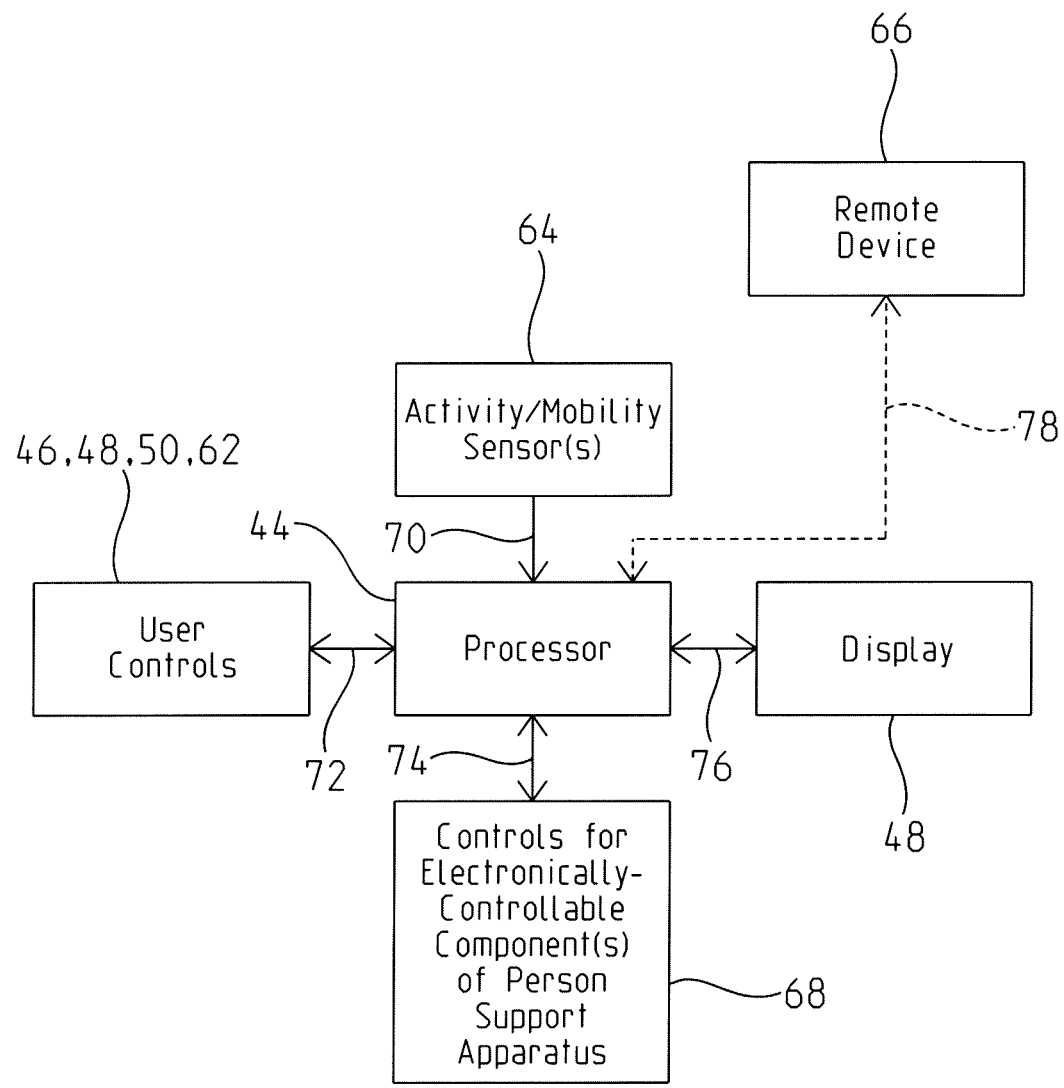
FIG. 2 is a simplified block diagram illustrating a system for conducting activity and/or mobility sensing and controlling electronically-controllable features of a person support apparatus.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

This disclosure is directed to automated methods and systems for assessing the activity and/or mobility of a person while that person is situated on a person support apparatus, and using the person's activity and/or mobility information to configure the person support apparatus. "Mobility," as contemplated by this disclosure, refers to the person's ability to offload themselves, or make relatively minor changes in the position of their body, or an extremity thereof, while they are supported by a person support apparatus, without assistance from another person. Some examples of changes in position that would typically be representative of a person's mobility include rolling from one's side onto the back or front, rolling from the back or front onto one's side, lifting or turning the head, raising or lowering an arm or leg, bending a knee or elbow, and flexing a foot or wrist.

A person's mobility can be used to assess the person's risk of developing a health condition. A higher mobility score may indicate a higher risk of developing a health condition such as pressure sores or hip fractures (and thus, lower mobility), while a lower mobility score may indicate a higher degree of mobility, and thus, a lower risk of the person developing a health condition. For example, a mobility score of "10" may indicate that a person is completely immobile, i.e. unable to make even slight changes in the position of the body or an extremity without assistance. A mobility score of "6" may indicate that a person's mobility is very limited, but the person is not completely immobile. In other words, the person is able to make occasional slight changes in position of the body or extremity, but is unable to make frequent or significant changes, without help. A mobility score of "3" may indicate that the person's mobility may be only slightly limited, i.e., the person is able to make frequent, though slight, changes in the position of the body or an extremity, without assistance. A mobility score of "0" may indicate that the person may have no limitations relating to mobility. In other words, the person is able to make major and frequent changes in position, without assistance. In other embodiments, a lower mobility score may indicate a low degree of mobility, while a high mobility score indicates a high degree of mobility (e.g. a mobility score of "1" indicates low mobility, high health risk, while a mobility score of "10" indicates high mobility, low health risk).

Thus, an assessment of a person's mobility can include both an assessment of the degree of a change in position (e.g. the significance of a change in position, for example, whether the person moved from a laying down to a sitting up position or simply raised their head), and an assessment of the frequency of such changes in position (e.g. how often a person makes even minor changes in position).

Mobility may be considered separately from the person's activity level. For example, a person's activity level may be quantified as a separate risk factor that indicates the degree of larger-scale physical activity a person is able to perform independently. The activity score typically contemplates an assessment of larger-scale movements. For example, a low activity score may indicate that a person is incapable of making the gross movements required to lift themselves out of bed. Higher activity scores may indicate varying levels of ability relating to ambulation once the person is out of bed (e.g., whether the person requires a wheelchair or is able to walk independently). In other embodiments, a low activity score may indicate low health risk, high activity, while a high activity score may indicate high health risk, low activity.

The Braden Scale is one example of a scoring methodology that utilizes activity and mobility information. Information about the Braden Scale is available at www.bradenscale.com. It will be understood that other forms and types of scoring methods using activity and/or mobility information also exist or may be developed. Thus, while this disclosure mentions the Braden Scale as one example, this disclosure does not require the use of the Braden Scale or any other particular form or type of scoring methodology.

Mobility and activity scores can be used together to provide a more complete assessment of a person's health status. Even if a person is unable to walk (therefore having a relatively low activity score), that person may still be able to make major movements without assistance, and therefore have a higher mobility score. This may be the case with some wheelchair athletes, for example. Whereas a low activity score by itself may be an indicator of an increased risk of developing pressure sores, a high mobility score may suggest that the risk is not as great as it would be for a person with the same activity score but a lower mobility score. In some cases, a person who would otherwise be considered a high risk for developing pressure sores might not be so considered, due to their mobility score.

Similarly, even if a person is able to walk, and therefore has a higher activity score, the person may not otherwise be able to exert significant control over their body movements without assistance. For example, persons with neurological disorders or diseases such as Alzheimer's or related diseases may be unable to lift their arms or legs, or raise their head, independently, due to their cognitive impairment. Thus, in some cases, a lower mobility score might be sufficient to classify a person as being at a "high risk" for developing pressure sores, even though the person's activity score is higher.

Often, caregivers or other staff may assess a person's activity and/or mobility by performing visual observation. While informative, visual observation has several drawbacks. Visual observation can be time-consuming and may lack objectivity, particularly over a period of time. For busy caregivers who are in constant demand, the ability to make accurate and consistent observations for each person needing to be monitored may be compromised. In accordance with this disclosure, automated methods and processes can be used with available sensor technology to assess and/or monitor a person's activity and/or mobility, while the person is positioned on a person support apparatus.

One exemplary person support apparatus 10 is shown in FIG. 1. Although shown in a horizontal position, the person support apparatus 10 is designed to support a person in a seated position, a laying-down position, and a variety of other positions. The person support apparatus 10 is of a type that is typically used in hospitals and/or other facilities in which health care is provided. However, this disclosure applies to any type of person support apparatus or similar structure, including but not limited to beds, mattresses, cushions, tables, stretchers, chairs, wheelchairs and other person support structures, whether or not all of the features of the illustrated person support apparatus 10 are included in such structure, and whether or not such person support structure includes other features not mentioned herein.

The person support apparatus 10 has a head end 14 and a foot end 16 longitudinally spaced from the head end 14. The person support apparatus 10 includes a base 12. The base 12 is movably supported by a pair of head end casters 38 (view of one caster obstructed) and a pair of foot end casters 40. The casters 38, 40 each include one or more wheels that movably support the person support apparatus 10 relative to a floor or other surface, in one or more directions.

A frame 20 is coupled to and supported by the base 12. A lift mechanism, which includes a pair of head end lift arms 22 and a pair of foot end lift arms 24, is coupled to the base 12 and to the frame 20. The lift arms 22, 24 operate to raise, lower, and tilt the frame 20 relative to the base 12. Movement of the lift arms 22, 24 is driven by electronically-controllable actuators, such as, for example, linear actuators (not shown).

A deck 18 is coupled to and supported by the frame 20. The deck 18 supports a mattress 52, which, in turn, may support a person positioned thereon. The deck 18 has a number of sections including, in the illustrated embodiment, an articulating head section 54 and an articulating foot section 56, which pivot relative to the frame 20, to allow the person support apparatus 10 to assume a variety of positions including a horizontal position, a chair position, a low position, in which the frame 20 is lowered toward the base 12, a Trendelenburg position, a Reverse Trendelenburg position, and a number of positions intermediate the horizontal and chair positions. Pivoting of the deck sections (e.g. 54, 56) is driven by electronically-controllable actuators, such as, for example, linear actuators (not shown).

The person support apparatus 10 has a number of siderails, namely opposing head end siderails 26, 28 and opposing foot end siderails 30, 32. At least the foot end siderails 30, 32 have a latching mechanism 58, 60 that allows them to be lowered below the height of the top of the mattress 52. When a foot end siderail 30, 32 is lowered, a person may exit the person support apparatus 10 from the side of the person support apparatus 10. The person support apparatus 10 also has a head endboard 34 and a foot endboard 36.

The person support apparatus 10 has one or more electronically-controllable bed functions or features, which are operated by a control unit or processor 44. Such features may include, but are not limited to: adjusting the position, length, or width of the bed, raising, lowering, or pivoting a section or sections of the bed, weighing a person positioned on the bed, inflating, deflating, or adjusting inflation in one or more sections of the mattress, laterally rotating a person positioned on the bed, providing percussion, vibration, pulsation, or alternating pressure therapy to a person positioned on the bed, adjusting airflow through a portion of a mattress or topper, monitoring a person's position or orientation on or relative to the bed, generating an alert if a person on the bed changes position or exits the bed or is in a certain position for too long, weighing a person positioned on the bed, enabling a person positioned on the bed to communicate with a caregiver located outside the person's room through an electrical network or telecommunications system, and exchanging data and/or instructions with other devices, equipment, and/or computer systems (such as a nurse call system or workflow system), and/or other automated features. Accordingly, the person support apparatus 10 has its own supply of electrical power (e.g. a battery) and/or a connector (not shown) that connects the person support apparatus 10 to a supply of AC electrical power (e.g. a wall outlet).

As noted above, the person support apparatus 10 has a number of powered actuators, such as electric linear actuators or hydraulic cylinders, or other similar devices, which enable the person support apparatus 10 or portions thereof to assume different positions. One or more actuators are coupled to the frame 20 as needed to enable raising, lowering, and tilting of the frame 20 relative to the base 12. Other actuators are coupled to the deck sections (e.g. 54, 56) as needed, to enable pivoting of the deck sections (e.g. 54, 56) relative to the frame 20. Some examples of actuators are disclosed in U.S. Pat. Nos. 5,715,548; 6,185,767; 6,336,235; 6,694,549; 7,454,805; 6,708,358; 7,325,265; 7,458,119; 7,523,515; 7,610,637; 7,610,638; and 7,784,128.

In general, each of the actuators is coupled to a drive unit (e.g. a motor) and has an extending/retracting arm or linkage. One end of the arm or linkage is coupled to the drive unit and the other end is coupled to the frame 20 or the relevant deck section (e.g. 54, 56). The drive unit drives the arm or linkage in one direction to provide movement of the frame 20 or deck section (e.g. 54, 56) in one direction (e.g. raising or pivoting upwardly), and drives the arm or linkage in the opposite direction to provide movement of the frame 20 or deck section (e.g. 54, 56) in the other direction (e.g. lowering or pivoting downwardly). The drive unit is responsive to control signals issued by the processor 44. When movement of the frame 20 or a deck section (e.g. 54, 56) is requested, the processor 44 may determine the duration of the requested movement (i.e. how far the associated arm or linkage is to be extended or retracted, as the case may be) and/or the speed at which the requested movement is to be accomplished (i.e. how slowly or quickly the associated arm or linkage is to be extended or retracted). The processor 44 then sends corresponding control signal or signals to the appropriate drive unit.

The person support apparatus 10 may include one or more sensors that are coupled to the actuators and configured to monitor the speed or progress of movement or articulation of a frame or deck section of the person support apparatus. For example, a bed-not-down sensor may be coupled to the foot section 56 and/or to the lift mechanism 22, 24, to alert a caregiver if the person support apparatus 10 is in a position that is not suitable for egress, or for other reasons. In response to signals from a bed-not-down sensor, the processor 44 may issue a visual and/or audible signal and/or communication signal indicating that the person support apparatus 10 or a section thereof is not in its low or 'down' position.

The person support apparatus 10 may be equipped with sensors that are configured to detect other conditions. For example, one or more position sensors (e.g. force sensors) may detect force applied to the person support apparatus 10 at different locations on the bed. In such event, the processor 44 includes executable instructions that determine, based on the output of the force sensor or sensors, the position of a person relative to the bed (e.g. that the person has exited the bed, is on the edge of the bed, or is sitting up in bed). The processor 44 may then issue a visual and/or audible signal and/or communication signal relating to the person's position. Some examples of person support apparatuses having person position monitoring features are disclosed in U.S. Pat. Nos. 6,067,019; 6,133,837; 6,208,250; 6,791,460; and 7,464,605. Some examples of types of sensors that may be used for person position monitoring include load cells, which may coupled to the frame 20 or a deck section (e.g. 54, 56), pressure sensors, force sensors (e.g. tape switches), or optical sensors, which may be coupled to the mattress 52, and angle sensors (e.g. inclinometers, accelerometers, ball switches), which may be coupled to the frame 20, a deck section (e.g. 54, 56), or the mattress 52.

In accordance with this disclosure, the processor 44 may enable a caregiver to turn person position monitoring features on or off for a particular person, or to configure a person position monitoring feature, based on the person's activity and/or mobility assessment. For example, for one person, processor 44 may configure the person position monitoring feature to only send an alert if the person has exited the bed, while for another person, the processor 44 may configure the person position monitoring feature to send an alert if the person is detected as sitting on the edge of the bed or if the person has exited the bed, based on the persons' activity and/or mobility assessments.

The person support apparatus 10 may be equipped with one or more angle or orientation sensors, such as ball switches, potentiometers, inclinometers, accelerometers, or the like, which detect changes in the orientation of the bed or one section of the bed relative to another section of the bed. For example, an orientation sensor may be used to determine the angle of the head section 54 or the foot section 56 of the bed relative to the bed frame 20 or to the horizontal. In such event, the processor 44 includes executable instructions that determine, based on the output of the orientation sensor or sensors, the orientation of the bed or a section thereof. The processor 44 may then issue a visual and/or audible signal and/or communication signal relating to the bed's orientation. For example, the processor 44 may alert a caregiver if the angle of the head section 54 is less than 30 degrees above horizontal. One example of a person support apparatus that has a head angle alarm feature is disclosed in U.S. Pat. No. 7,487,562.

In accordance with this disclosure, the processor 44 may turn head angle monitoring features on or off for a particular person, or configure a head angle monitoring feature, based on the person's activity and/or mobility assessment. For example, for one person, the processor 44 may configure the head angle monitoring feature to send an alert if the head angle of the bed has been less than 30 degrees for a certain length of time, while for another person, the processor 44 may configure the head angle monitoring feature to send an alert if the head angle of the bed has been less than 30 degrees for a different length of time.

The person support apparatus 10 may be equipped with one or more pressure sensors, such as transducers, strain gauges, capacitive, optical or piezoelectric sensors, or the like, which detect changes in pressure applied to different sections of the mattress 52 or pressure inside of the mattress 52 (if the mattress 52 has air bladders).

In such event, the processor 44 includes computer-executable instructions that determine, based on the output of a pressure sensor or sensors, the pressures within air bladders or zones of air bladders of the mattress 52. The processor 44 may then determine that a bed condition has occurred based on the pressure sensor output, such as a bottoming out condition or a max-inflate condition. The processor 44 may alternatively or in addition issue control signals to inflate or deflate the mattress 52 or certain air bladders based on the output of the pressure sensors, as may be the case when the bed is operating in a pressure relief mode or a therapy mode. The processor 44 may issue a visual and/or audible signal, and/or a communication signal relating to the mattress condition or status. Some examples of person support apparatuses having sensors responsive to mattress conditions are disclosed in U.S. Pat. Nos. 6,505,368; 7,260,860; 7,330,127; 7,469,436; and 7,617,555.

In accordance with this disclosure, the processor 44 may turn a particular mattress feature on or off for a particular person, or configure a particular mattress feature, based on the person's activity and/or mobility assessment. For example, the processor 44 may set maximum and minimum pressures, rotation angles, percussion or vibration parameters, cycle times or therapy duration times differently based on a person's activity and/or mobility assessment.

The mattress 52 may be, or may include, a low airloss device, such as a cushion, enclosure, or topper. Generally speaking, a "low airloss" feature allows air to escape the mattress (or other support surface) in a purposeful way, for the purpose of cooling the person situated thereon, reducing the risk of pressure ulcers, wicking away moisture, or for other reasons. Airflow through the low airloss device may be driven by a powered device, such as a vacuum or blower. In such event, the processor 44 includes computer-executable instructions that control the turning on and off of the airflow, determine and adjust the airflow setting (e.g. the speed of the vacuum or blower device), and/or determine and adjust the temperature of the airflow. The processor 44 may issue a visual and/or audible signal, and/or a communication signal relating to the current setting or status of the low airloss device or its airflow. Some examples of low airloss systems are disclosed in U.S. Pat. No. 5,647,079 and U.S. Patent Application Pub. Nos. 2007/0266499 and 20110024076.

In accordance with this disclosure, the processor 44 may turn a low airloss feature on or off for a particular person, or configure a low airloss feature, based on the person's activity and/or mobility assessment. For example, the processor 44 may set the vacuum/blower speed parameters, cycle times, low airloss therapy duration times, or airflow temperatures differently for different persons, based on the activity and/or mobility assessment.

A proximity sensor, switch, or other suitable device may be coupled to one or more of the siderails 26, 28, 30, 32, and to the processor 44 to detect whether the siderails are up or down. The processor 44 may then issue a visual and/or audible signal and/or communication signal relating to the status of the siderails 26, 28, 30, 32. For example, the processor 44 may alert a caregiver if one or more of the siderails 26, 28, 30, 32 are down and a person is on the person support apparatus 10. An example of a person support apparatus having a siderail down sensor is disclosed in U.S. Pat. No. 6,021,533.

In accordance with this disclosure, the processor 44 may turn the siderail monitoring features on or off for a particular person, or configure the siderail monitoring feature, based on the person's activity and/or mobility assessment.

The above-described electronically controllable features of the person support apparatus 10 are intended to be illustrative and non-exhaustive. It will be understood that other electronically controllable features of the person support apparatus 10 not mentioned herein may be configured in accordance with a person's activity and/or mobility assessment in a similar manner.

The sensor(s) with which the person support apparatus 10 is equipped may output data signals in discrete or continuous, analog or digital form. The person support apparatus 10 is equipped with appropriate signal processing circuitry and/or devices (e.g. analog-to-digital converters, digital-to-analog converters, filters, and the like) to enable the communication of signals between each of the sensors and the processor 44 and the processing of the signals by the processor 44.

The electronically-controllable features and functions of the person support apparatus 10 may be activated, configured, and deactivated by user inputs that are translated into electrical signals and forwarded to the processor 44 by input devices or input-output devices such as foot pedals, buttons, switches, dials, slides, and the like, as well as graphical user interface modules and/or touchscreens.

For example, the person support apparatus 10 has a number of foot pedals 62. The foot pedals 62 are coupled to and supported by the base 12. The foot pedals 62 are in electrical communication with the processor 44 and may be used by a caregiver to change the position of the person support apparatus 10, or to control the casters (e.g. activate or deactivate a brake or steer lock mechanism), or to activate or deactivate some other feature of the person support apparatus 10. Stepping on a foot pedal issues a control signal to the processor 44, using existing or newly developed techniques. Some examples of person support apparatuses with foot-operated controls are disclosed in U.S. Pat. Nos. 6,691,346; 6,978,500; and 7,171,708.

The person support apparatus 10 also has a caregiver input-output device 46, 48 and a user input-output device 50, which are configured to permit caregivers and persons, respectively, to activate and deactivate certain electronically-controllable features of the person support apparatus 10 using their hands, fingers, or a hand-held instrument.

The caregiver input-output device 46, 48 receives and processes electrical input (e.g. voltage) from one or more controls mounted thereto, which enable a caregiver to configure, activate and/or deactivate certain of the electronically-controllable functions. For example, some person support apparatuses permit the caregiver to raise and lower the person support apparatus or change the position of certain sections thereof, change the length or width of the person support apparatus; or to achieve a chair, CPR, Trendelenburg, or reverse Trendelenburg position; or to activate certain mattress therapies (such as lateral rotation, percussion, or vibration), by physically contacting the selected control. The device 46 includes buttons or other hardpanel controls. The device 48 is a graphical touchscreen user interface that has a number of menus and caregiver controls that allow a caregiver to activate, deactivate, or configure features of the person support apparatus 10.

The caregiver input-output device 46, 48 includes circuitry configured to convey voltage generated by the controls mounted thereto to the processor 44. In the illustrated embodiment, a caregiver input-output device 46, 48 is mounted to the outwardly facing side of at least one of the siderails 30, 32 of the person support apparatus 10 (i.e., facing away from the mattress 52), but the caregiver input-output device 46, 48 may be placed in any suitable location that is accessible to a caregiver. For example, some caregiver controls may be provided on a wall-mounted device or remote control device.

The user input-output device 50 receives and processes electrical input (e.g. voltage) from number of manually operable controls (such as membrane switches, keys, dials, levers, or the like), which enable a person to activate and deactivate certain features or functions when the person is positioned on the person support apparatus 10. For example, some person support apparatuses permit the person to raise and lower the person support apparatus or change the position of certain sections thereof by touching these controls.

The user input-output device 50 includes circuitry to convey voltage generated by the manually operable controls to the processor 44. In the illustrated embodiment, a user input-output device 50 is mounted to the inwardly facing side of at least one of the siderails 30, 32 of the person support apparatus 10 (i.e., facing toward the mattress 52), but the person input-output device 50 may be placed in any suitable location that is accessible to a person using the person support apparatus 10. For example, some person controls may be provided on a pendant controller or remote control device.

The processor 44 includes one or more microprocessors or microcontrollers and electrical and/or computer circuitry mounted on one or more substrates (e.g. printed circuit boards), which are typically located in a housing that is mountable to the person support apparatus 10. In the illustrated embodiment, the processor 44 is mounted to the base 12. However, the processor 44 may be placed in any suitable location on the person support apparatus 10 or elsewhere. The location of the processor 44 relative to the person support apparatus 10 is not important for the purposes of the present disclosure.

The person support apparatus 10 is equipped with one or more sensors 64 that are configured to detect "minor" changes in the position of a person's body or an extremity that are indicative of a person's mobility, while the person is positioned on the person support apparatus, where the "minor" changes in position are more significant in degree than physiological functions of the person (such as breathing or heart rate). Any of the aforementioned types of sensors, or groupings or arrays thereof, may be used to detect such position changes, as long as the desired range of position changes can be detected without being confused with physiological signals or with "major" position changes (such as bed exit or sitting up).

The processor 44 receives electrical input from the sensor(s) 64, the user controls 46, 48, 50, 62, and component controls 68, and provides output via the display 48 and optionally, via a remote device 66, and provides controls signals to the component controls 68, via a number of signal paths 70, 72, 74, 76, 78. The processor 44, user controls 46, 48, 50, 62, sensor(s) 64 and signal paths 70, 72, 74, 76, 78 are arranged according to a suitable system architecture (such as a peer-to-peer architecture, a Controller Area Network, or other suitable architecture now existing or developed after the date of this disclosure) to allow unidirectional and/or bidirectional electrical communication among these and other components as required to execute the electronically controllable features and functions of the person support apparatus 10.

The signal paths 70, 72, 74, 76, 78 may include wired or wireless connections, or may be connected to an electronic network, such as an Ethernet network, which may be configured according to a TCP/IP or other suitable electronic communications protocol. In general, each of the representative signal paths 70, 72, 74, 76, 78 may include one or more signal paths therein as may be needed to accomplish the sending and receiving of data and/or instructions between or among the various modules and systems.

Among other things, the processor 44 processes inputs, stores data in and retrieves data from memory, and executes computer logic to control the operation of the various electronically-controllable features of the person support apparatus 10. Similarly, the component controls 68 process inputs (e.g. from the processor 44), may store data in and retrieve data from memory, and execute computer logic to control the operation of a particular component (e.g. an actuator, motor, display, air supply, valve, vacuum/blower, brake, or latch) of the person support apparatus 10 that is electronically-controllable.

The logic, functions and processes identified herein as being part of the processor 44 or the component controls 68 may be implemented as one or more separate modules that are in communication with the processor 44 or may be entirely incorporated into the processor 44. Additionally, the processor 44 itself may be implemented as a single module or a number of distributed modules.

Figure 3:
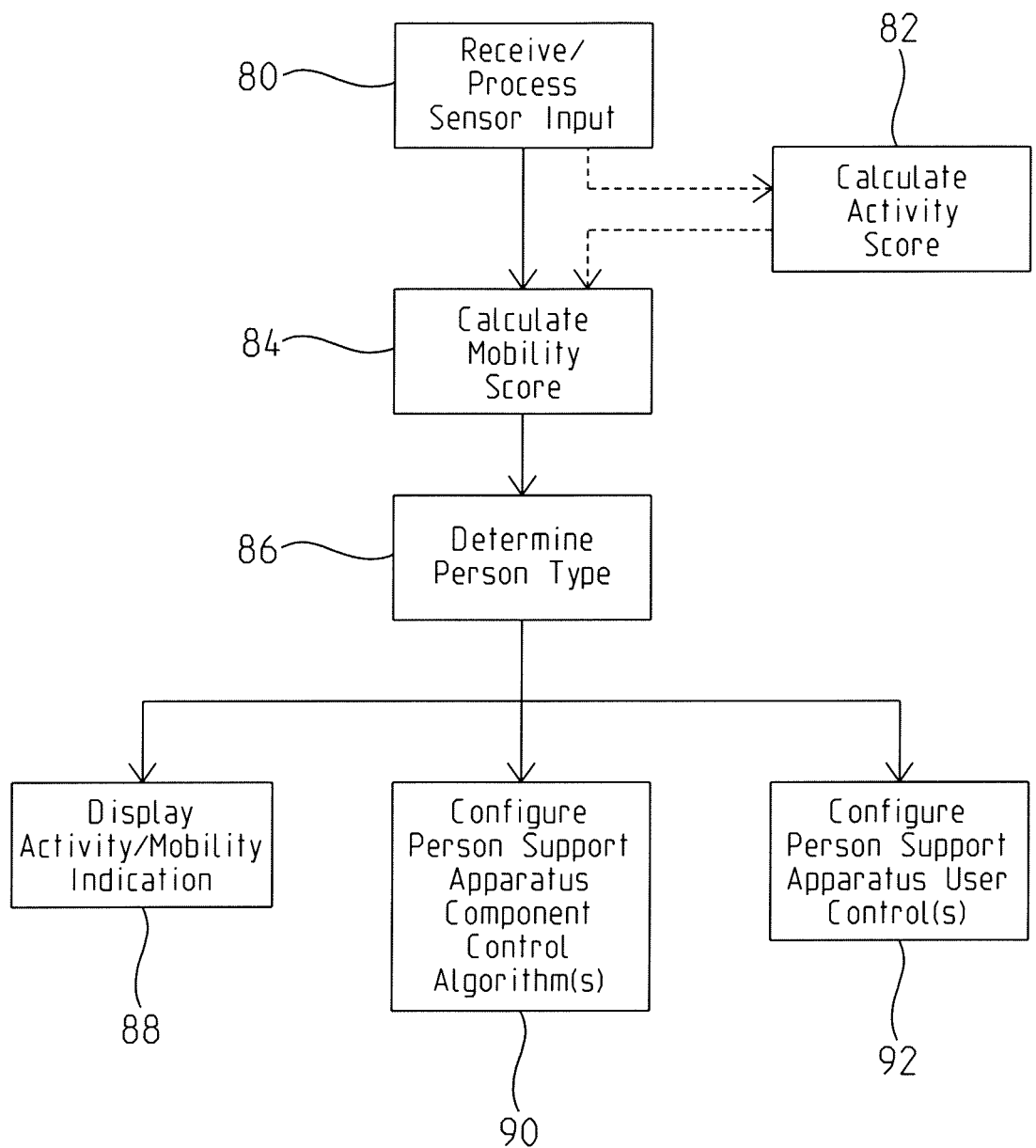
FIG. 3 is a flow diagram illustrating a process for using activity and/or mobility sensing to configure features of a person support apparatus.

FIG. 3 illustrates steps or routines of a process that may be implemented using computer circuitry and/or programming, stored in memory, and executed by the processor 44 and/or the component controls 68 to perform an activity and/or mobility assessment for a person positioned on a person support apparatus and, if desired, control one or more electronically-controllable features of the person support apparatus 10 based on the person's activity and/or mobility assessment.

At block 80, sensor inputs, i.e. signals from the sensor(s) 64, are received and processed over a defined period of time, which is monitored by a clock in electrical communication with the processor 44. Conventional and/or newly developed sampling, filtering and/or signal conditioning algorithms are applied to the sensor inputs as needed to eliminate noise and other extraneous elements. The sensor inputs are stored in computer memory at the processor 44.

The clock output, e.g. a time stamp indicating the date/time at which each input was generated, is associated with each input and stored in memory. The time interval over which sensor inputs are collected to evaluate a person's mobility is defined to capture changes in position that are commonly associated with a person's mobility, rather than movements that typically indicate physiological activity or major changes in position that are more typically associated with a person's activity level (e.g. sitting up, exiting the bed). Whereas monitoring of physiological sensor inputs may take place over a short time interval (e.g. 10 seconds to 1 minute for heart rate), a longer time interval is used for the monitoring of mobility sensor inputs.

Figure 6:
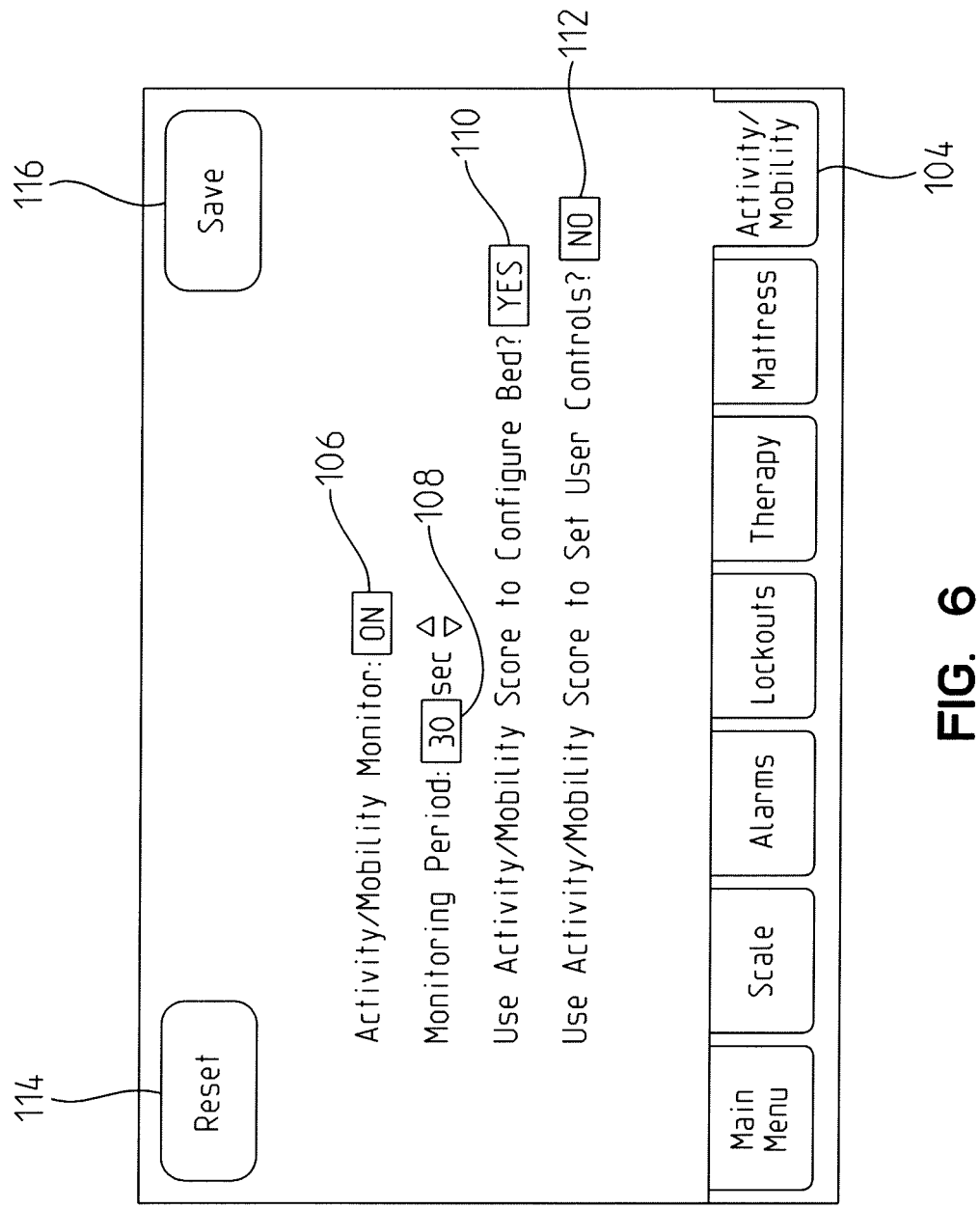

Since a person may enter or exit a person support apparatus at any time, an even longer time interval (e.g. in the range of a number of hours) is typically used for the monitoring of activity sensor inputs. Thus, the time interval used for monitoring mobility sensor inputs is longer than the time interval used for physiological monitoring and typically shorter than or equal to the time interval used for activity monitoring. More specifically, mobility monitoring may occur only while the person has been detected as being situated on the person support apparatus 10, while activity monitoring may continue after the person has exited the bed, in order to detect the return of the person to the bed. In one embodiment, the time interval for monitoring mobility sensor inputs is in the range of about 30 minutes, but could be longer, if the person is bedridden, for example. FIG. 6 illustrates an example user interface 48, which allows an authorized person (e.g. a caregiver) to configure the activity and/or mobility monitoring feature and set the monitoring time period 108.

Once the sensor inputs have been collected and processed for the applicable monitoring time period, they may be used to calculate the person's activity score at block 82. The process of calculating an activity score is optional, as is indicated by the dashed lines on FIG. 3, however, it may be used to determine when to turn on mobility monitoring or when to start the time period for calculating the mobility score of block 84, discussed below. For instance, activity monitoring may occur continuously while the person support apparatus 10 is powered on, however, mobility monitoring might not begin until a person is detected on the person support apparatus 10. Other methods of determining when to initiate mobility monitoring may also be used. For instance, if the person support apparatus 10 is equipped with an on-board weigh scale, a positive reading in the range of the person's weight may be used to start mobility monitoring. Also, as shown in FIG. 6, an authorized person may turn the activity and/or mobility monitoring feature on or off via the user interface 48, at the area 106.

At block 82, an activity score is calculated for the person situated on the person support apparatus 10. The activity score is a function of the changes in magnitude of the sensor inputs over the typically longer time interval defined for activity monitoring. Larger changes in magnitude indicate more significant changes in position, which are associated with activity rather than mobility. Thus, at block 82, the algorithm analyzes the number and frequency of larger changes in magnitude of the sensor inputs over the defined activity monitoring time interval. In one embodiment, in which load cells located at each of the four corners of the person support apparatus 10 are used to detect changes in the person's position by correlating them to changes in weight distribution among the load cells, the analysis may include summing the values obtained from the four load cells. The applicable magnitude range for the activity analysis may vary from person to person, based on the person's weight, body type, or other factors, and therefore may be "learned" by the algorithm over an initial period of time in which the system is calibrated. Since the activity-related position changes often differ from mobility-related position changes by an order of magnitude or more, the analysis may also include multiplying the values by a scalar, which may be determined through laboratory testing.

The algorithm then derives an activity score from the activity data. The activity score is a value or plurality of values representing the person's level of activity over the monitored period. The activity score is derived by mapping the results of the analysis of the sensor inputs to threshold values that are indicative of different activity levels. The threshold values and corresponding activity scores are stored in computer memory at the processor 44 (e.g. as a lookup table).

The threshold values are determined through laboratory testing. For example, in the load cell embodiment, sensor inputs that indicate that each load cell is at about 50% of its dynamic range may indicate that a person is on the person support apparatus 10 and is not moving. For activity monitoring, at least one threshold value, that which indicates a person has entered the person support apparatus 10, is used. However, it will be understood that additional activity thresholds may be defined to associate the sensor inputs as being indicative of other major activity of the person situated on the person support apparatus 10.

A scoring system may be used to determine the activity score corresponding to the sensor inputs. For instance, a number of large changes in magnitude of the sensor inputs over a relatively short period of time (e.g. 1 hour) may indicate that the person has been able to enter, lay down, sit up and exit the bed within that time period. Such data may indicate that the person is not bedridden and therefore should be assigned a higher activity score.

At block 84, a mobility score is calculated for the person situated on the person support apparatus 10. The mobility score is a function of the changes in magnitude of the sensor inputs over the time interval defined for mobility monitoring. Changes in magnitude that are smaller than those associated with activity monitoring, but larger than those associated with physiological monitoring, are used to assess the person's mobility. Thus, at block 84, the algorithm analyzes the number and frequency of changes in magnitude of the sensor inputs over the defined mobility monitoring time interval, focusing on sensor inputs that have a magnitude in the range that indicates mobility rather than activity or physiological signals. The applicable magnitude range for the mobility analysis may vary from person to person, based on the person's weight, body type, or other factors, and therefore may be "learned" by the algorithm over an initial period of time in which the system is calibrated.

Mathematical techniques may be used to differentiate between mobility-related movements and activity-related movements, or to quantify the assessment of the person's activity and/or mobility as an activity and/or mobility score, or to filter out noise, or for other reasons. In some embodiments, the mobility algorithm calculates the mean and the standard deviation of the sensor inputs obtained over the defined mobility time interval. In other embodiments, a rolling derivative is used to distinguish between larger-scale changes in position that are indicative of activity and smaller-scale changes in position that are indicative of mobility. In still other embodiments, other techniques may be used, including but not limited to integration, Fast Fourier Transform (FFT), and coefficient of variation, to name a few.

Since the mobility-related position changes often differ from activity-related position changes by an order of magnitude or more, the analysis may also include multiplying the values by a scalar, which may be determined through laboratory testing.

The algorithm then derives a mobility score from the mobility data. The mobility score is a value or multiple values representing the person's level of mobility over the monitored period. The mobility score is derived by mapping the results of the analysis of the sensor inputs to threshold values that are indicative of different mobility levels. The threshold values and corresponding mobility scores are stored in computer memory at the processor 44 (e.g. as a lookup table).

The threshold values may be determined through laboratory testing and modified during the calibration period. At least one threshold value is defined for the mobility analysis, such that if the calculated mobility value is lower than the threshold mobility value, the person is considered as having poor or low mobility, and if the calculated mobility value is higher than the threshold mobility value, the person is considered as having good or high mobility. However, it will be understood that additional mobility thresholds may be defined to associate the sensor inputs as being indicative of finer degrees of mobility of the person situated on the person support apparatus 10. Also, it will be understood that calculated values exceeding the threshold values may indicate low mobility, rather than high mobility, and vice versa, depending upon the particular mathematical techniques or scoring systems that are used in particular designs.

A scoring system is used to determine the mobility score corresponding to the calculated mobility value. For instance, a number of changes in magnitude of the sensor inputs over a relatively short period of time (e.g. 10-30 minutes) may indicate that the person has been able to adjust their position on the person support apparatus 10 without assistance during that time period. Such data may indicate that the person is not completely immobile and therefore should be assigned a higher mobility score.

If both an activity score and a mobility score are determined, the algorithm may use one or more mathematical operations (e.g. addition, subtraction, multiplication, division, etc.) to calculate a value that represents the activity and mobility assessments combined. Thus, references herein to "activity and/or mobility score" or "activity/mobility score" may refer to an activity score, or a mobility score, or a combined activity and mobility score.

Figure 4:
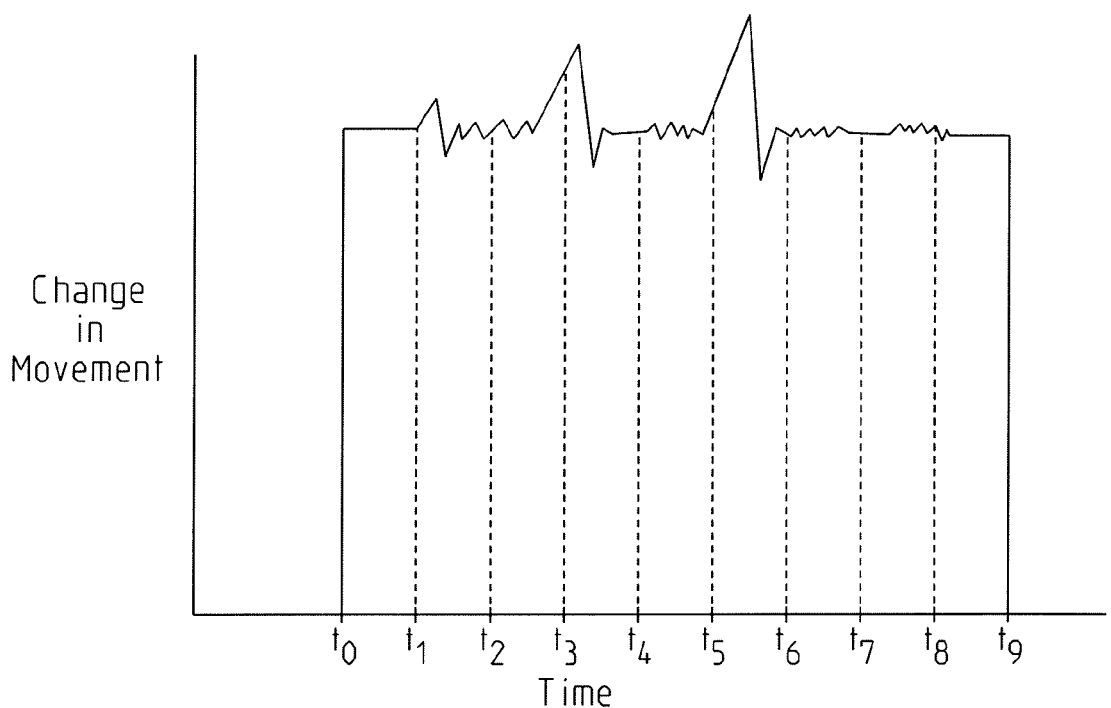
FIG. 4 is a simplified example of a chart illustrating the monitoring of activity and mobility over time.

FIG. 4 illustrates sensor inputs used for monitoring mobility and/or activity over time. At time t0, the change in magnitude and the direction of the change (positive) indicates that a person has entered the person support apparatus; thus, mobility monitoring can begin. From time t0 to t1, the amount of movement is below the minimum threshold for mobility monitoring. The changes in magnitude and the frequency of changes during the time intervals t1 to t2, t4 to t5, t6 to t7, and t7 to t8 represent changes in position that relate to the mobility analysis, while the changes in magnitude during the time intervals t3 to t4 and t5 to t6 relate more particularly to the activity analysis. At time t9, the change in magnitude and the direction of the change (negative) indicates that the person has exited the person support apparatus 10. All or a portion of the data collected during these time intervals may be used for activity and/or mobility monitoring.

Figure 5:
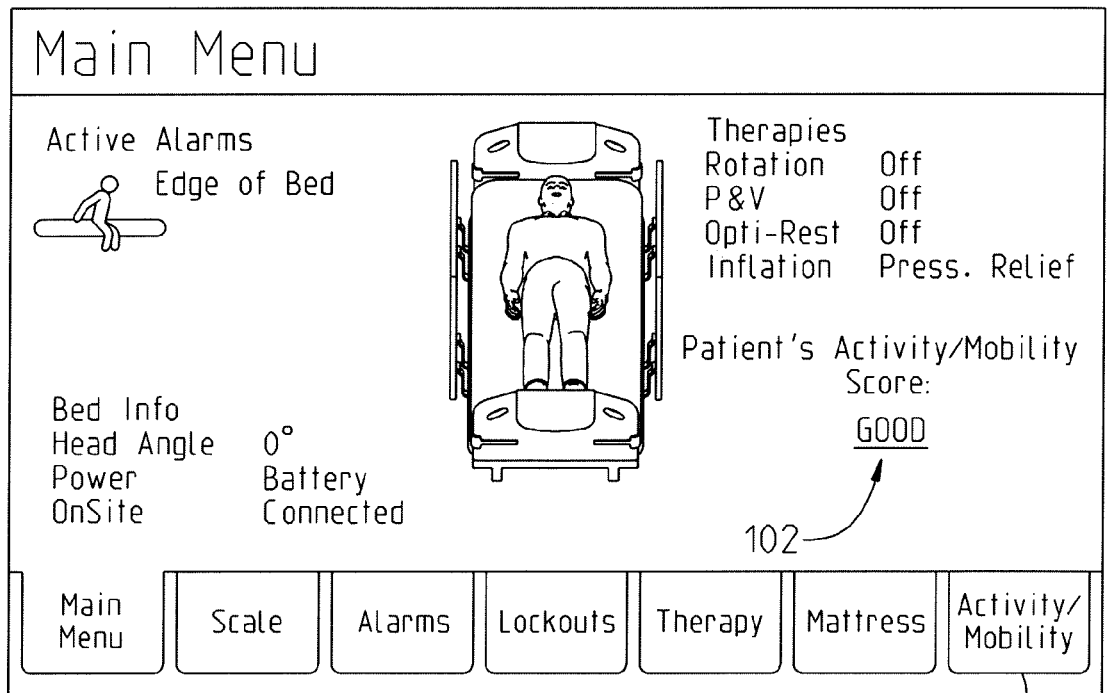
FIGS. 5-6 are simplified user interface screens for a person support apparatus, including functionality relating to a person's activity and/or mobility.

Once determined, the person's activity and/or mobility score may be displayed on the display 48 as indicated at area 102 of the exemplary user interface 100 shown in FIG. 5. An indicator of either the person's activity score or the person's mobility score, or both, may be displayed on the display 48. The person's mobility score and/or activity score may, alternatively or in addition, be communicated to a remote device 66 (such as a nurse's station, nurse call system, electronic status board, dome light, Vocera® device, smartphone, portable computing device, or other output device) via the communication link 78.

At block 86, the person's mobility score and (if determined) activity score are used to classify the person as being of a type that is or is not at risk of experiencing a health-related event, such as pressure sores or hip fractures. The association between mobility and activity scores, and person types, is defined by mapping the calculated scores to values stored in a lookup table, which is accessed by the processor 44. In one example, a low mobility score indicates that a person has a high risk of developing pressure sores while a high mobility score indicates that the person has a low risk of developing pressure sores, while in other examples, the opposite may be true. Thus, in this example, the person type would be either "high risk" or "low risk" depending on the mobility score. However, this disclosure contemplates that intermediate values may be used to indicate person types other than high or low risk (e.g. moderate risk), or that a continuum of values may be used. Also, this disclosure contemplates that factors other than mobility and activity may be included in the algorithm that determines the person type. For example, data relating to the person support apparatus 10 (such as head angle, bed position, or mattress firmness), or other factors, such as sensory capabilities, surface moisture, nutrition, shear, friction, or other applicable factors, may be input (e.g. at the user interface 48) and applied to the person type determination. Thus, the person type determination may be customized for the needs of a particular configuration of the person support apparatus 10.

Once a person type has been determined, the processor 44 may use the activity and/or mobility information in a number of ways to configure and operate the person support apparatus 10. At block 88, the activity and/or mobility indication of the person using the person support apparatus 10 is displayed, either at the person support apparatus 10 or at a remote device 66, as discussed above. Referring to FIG. 5, the exemplary screen 100 of the user interface 48 indicates the person's activity and/or mobility score 102 on the main menu screen. The person's activity score, mobility score, and/or person type, or all of these, may be displayed in a similar manner.

Referring to FIG. 6, area 110, an authorized person may set up the person support apparatus 10 to use the person's activity and/or mobility score to modify the operation of features or functions of the person support apparatus 10. These modifications may be made by the processor without any human intervention. If the person support apparatus 10 is so configured, the processor 44 modifies the person support apparatus component control algorithms 68 to account for the person's mobility score, activity score, and/or person type, at block 90. For example, if the person's activity and/or mobility score indicates high mobility, the processor 44 may disable the siderail down sensor, and/or disable the bed exit alarm, and/or increase the speed at which the actuators raise and lower portions of the person support apparatus 10, and/or disable or modify certain mattress therapies (such as continuous lateral rotation, percussion, vibration, turn assist, and the like), and/or disable or modify pressure relief features of the mattress 52.

Likewise, if the person's activity and/or mobility score indicates low mobility, the processor 44 may turn on the siderail down sensor, and/or turn on the bed exit alarm, and/or decrease the speed at which the actuators raise and lower portions of the person support apparatus 10 and/or make available certain mattress therapies (such as continuous lateral rotation, percussion, vibration, turn assist, pressure relief and the like).

Alternatively or in addition, the processor 44 may adjust the available ranges of operation for certain features of the person support apparatus 10 in response to the person's activity and/or mobility score, without human intervention. For instance, if the person's activity and/or mobility score indicates high mobility, the processor 44 may cause the rate of airflow through a low airloss surface to be increased or to include a broader range of vacuum/blower speeds, or cause the range of available temperatures of the airflow to include a broader range of available temperatures, or cause the mattress 52 to allow a broader range of pressures for inflation or deflation (to permit more firmness/softness options, for example), or permit a broader range of deck articulation options (allow the head section 54 to go below 30 degrees for example).

Likewise, if the person's activity and/or mobility score indicates low mobility, the processor 44 may cause the rate of airflow through a low airloss surface to be decreased or to include a smaller range of vacuum/blower speeds, or cause the range of available temperatures of the airflow to include a smaller range of available temperatures, or cause the mattress 52 to allow a smaller range of available pressures for inflation or deflation, or permit a smaller range of deck articulation options (to block the head section 54 from going below 30 degrees, for example), or require deck articulation to follow a particular sequence (to reduce shear, for example), such as raising the leg or thigh section 56 first, then raising the head section 54 after the person's legs or thighs have been raised.

Referring to FIG. 6, area 112, an authorized person may set up the person support apparatus 10 to use the person's activity and/or mobility score to modify the operation of one or more of the user controls 46, 48, 50. If the person support apparatus 10 is so configured, the processor 44 modifies the user controls 46, 48, 50 to account for the person's mobility score, activity score, and/or person type, at block 92. For example, if the person's mobility score indicates high mobility, the processor 44 may configure the person's user controls 50 so that a wider range of articulation, airflow or mattress pressure options are available, allow the person full control over pressure, articulation, or airflow adjustments, or make available certain user controls to be used that are not suitable for persons with lower mobility. Likewise, if the person's mobility score indicates low mobility, the processor 44 may configure the person's user controls 50 so that a smaller range of articulation, airflow, or mattress pressure options are available, or disable certain user controls that are not suitable for persons with low mobility (such as a chair position button, for example).

Referring again to FIG. 6, one or more touchscreen buttons 114, 116 are used to cancel or save changes made to the activity/mobility monitoring features of the person support apparatus 10, as the case may be.

Figure 7:
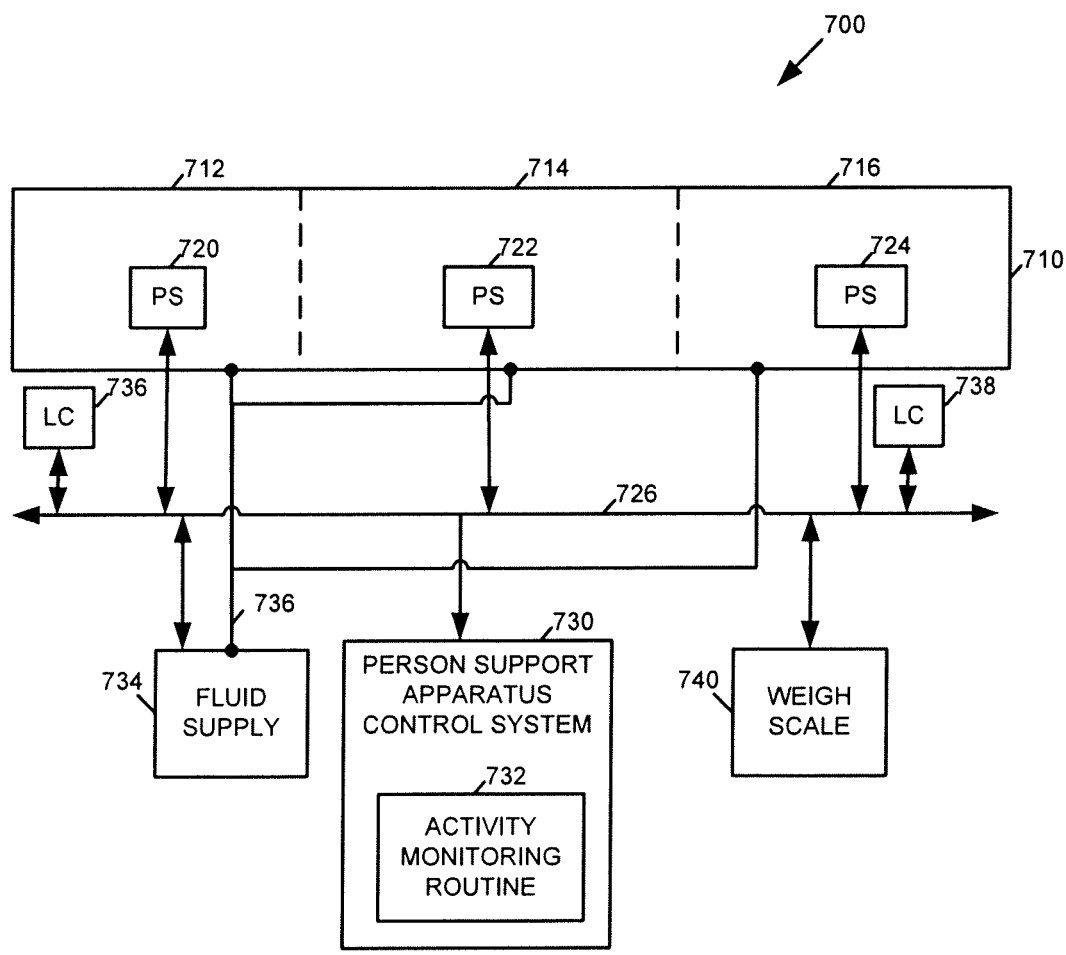
FIG. 7 is a simplified schematic of at least one embodiment of a person support apparatus having activity and/or mobility sensing features.

Referring now to FIG. 7, an illustrative person support apparatus 700 includes a person support surface 710. The person support apparatus 700 and the person support surface 710 may include any of the features or combinations of features described above in connection with the person support apparatus 10 and the mattress 52, and/or other features. The illustrative person support surface 710 includes a plurality of separately or independently controllable inflatable zones 712, 714, 716 (e.g., the fluid pressure within each zone 712, 714, 716 may be adjusted independently or separately, or in concert with, the others). In the illustrated embodiment, the zone 712 corresponds to a head section of the person support apparatus 700, which is configured to support at least the head of a person; the zone 714 corresponds to a seat section of the person support apparatus 700, which is configured to support at least a back, seat, thigh, and/or torso portion of a person; and the zone 716 corresponds to a foot section of the person support apparatus 700, which is configured to support at least the legs and/or feet of a person. While only three zones are illustrated in FIG. 7, it should be understood that the person support apparatus 700 may include any number of inflatable zones. In some embodiments, one or more sections or zones of the person support apparatus 700 may be articulated relative to the horizontal and/or relative to one or more of the other sections or zones of the person support apparatus 700. As an example, the head zone 712 may be pivoted upwardly relative to the horizontal in order to elevate the head and/or upper body of a person situated on the person support apparatus 700. Similarly, the seat zone 714 may be pivoted upwardly relative to the horizontal to elevate the thighs of a person situated on the person support apparatus 700, as the head zone 712 is being raised, for example. Likewise, the foot zone 716 may be pivoted downwardly relative to the horizontal or relative to the seat zone 714, to place the person support apparatus 700 in a chair or chair-like position, or to facilitate egress of a person from the person support apparatus 700, for example.

Each of the zones 712, 714, 716 includes at least one bladder that is operably coupled to a fluid (e.g., air) supply 734 via one or more fluid conduits 736 (e.g., plastic or flexible tubing). At least one pressure sensor 720, 722, 724 is operably coupled to the interior region of each of the zones 712, 714, 716 and/or the fluid conduit connected thereto. The pressure sensors 720, 722, 724 are configured to measure the internal fluid pressure in the zones 712, 714, 716 or individual bladders thereof, as the case may be. The pressure sensors 720, 722, 724 are operably coupled to a person support apparatus control system 730 by a communications network 726 (e.g., a Controller Area Network or CAN).

The illustrative person support apparatus control system 730 continuously monitors the internal air pressure of the zones 712, 714, 716 and interfaces with the fluid supply 734 via the network 726 to adjust (e.g., increase or decrease) the internal zone pressures according to one or more air pressure control routines, which may include a routine for managing or relieving interface pressures between portions of the person's body and the person support surface 710, a routine for providing one or more pulmonary therapies (such as percussion or vibration), a routine for alternating pressure increases and decreases in different zones or portions thereof, for lateral rotation, turning assistance, or other reasons, and/or other air pressure control routines.

The illustrative person support apparatus 700 also includes a number of force sensors 736, 738, which are coupled to a support frame of the person support apparatus 700 (e.g., frame 20 shown in FIG. 1). In some embodiments, the force sensors 736, 738 are embodied as load cells mounted at the four outer corners of the person support apparatus 700. Although only two force sensors 736, 738 are illustrated in FIG. 7, it should be understood that any number of force sensors may be used according to the requirements of a particular design of the person support apparatus 700. The force sensors 736, 738 are operably coupled to a weigh scale module 740 via the network 726. The illustrative weigh scale module 740 is embodied as a computerized module, which may be implemented in hardware, software, and/or a combination thereof, and, among other things, calculates the weight of a person positioned on the person support apparatus 700 based on the inputs from the force sensors 736, 738. Inputs from the force sensors 736, 738 may also be used to determine whether the person support apparatus 700 is occupied or vacant, or to determine the person's position on the person support apparatus 700 (e.g., laying down, sitting up, near an edge, etc.), in some embodiments.

The person support apparatus control system 730 can be embodied as a computing device including at least one hardware processor (e.g. a microprocessor or processor core), memory, and input/output devices and subsystems (e.g., network interfaces or other communications circuitry), configured to control electronically-controllable features of the person support apparatus 700, including control of the air pressure in the various zones 712, 714, 716, control of the weigh scale 740, among other things. An activity monitoring routine 732 is embodied as one or more computerized instructions or routines (as software, hardware, and/or a combination thereof) configured to execute one or more of the activity and/or mobility assessment routines described above with reference to FIG. 3, and/or one or more of the activity monitoring routines described below with reference to FIGS. 8-10.

Figure 8:
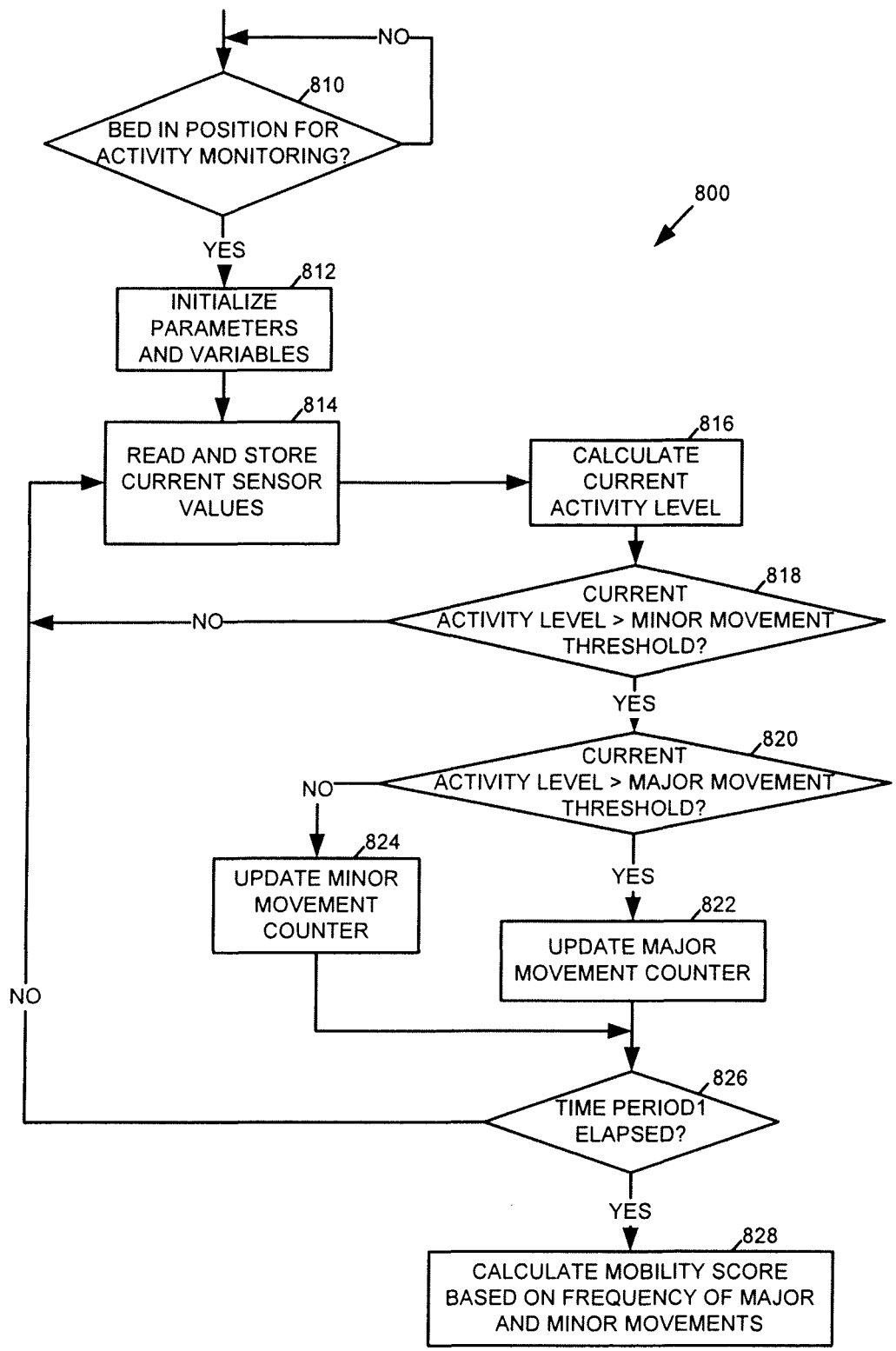
FIG. 8 is a simplified flow diagram of at least one embodiment of an activity monitoring routine.

Referring now to FIG. 8, a method 800 for monitoring the activity level of a person while the person is positioned on the person support apparatus 700 (e.g., in real time), and determining a mobility score based on the person's activity level, is shown. The method 800 may be implemented as computerized instructions executable by the processor 44 and/or the person support apparatus control system 730. The method 800 may be configured to detect and monitor "major" movements, "minor" movements, or combinations thereof, of a person situated on the person support apparatus 700 over time. Whether a movement is considered a major or minor movement is determined based on the calculation and evaluation of various parameters and variables, as described below. The person's activity level can be quantified as a mobility score, such as a Braden score. In this way, the method 800 can enable caregivers and others to assess the activity level and/or mobility of the person, directly at the person support apparatus 700 and based on automatically collected, objectively obtained information. In addition, the data collected, calculated and/or derived by the method 800 can be used by the person support apparatus control system 730, or by the caregiver directly, to detect events occurring at the bedside that may require the attention of the caregiver or an adjustment of the person support apparatus 700 (such as an increase or decrease in pressure in one or more of the zones 712, 714, 716, a change in the articulation of a zone 712, 714, 716, and/or a modification of some other feature or parameter of the person support apparatus 700.

At block 810, the illustrative method 800 determines (e.g., based on one or more inputs from various sensors or other electronically controllable components 68 of the person support apparatus 700), whether the person support apparatus 700 is in a position in which activity monitoring can be performed. In some embodiments, for example, the method 800 may require that the person support apparatus 700 is placed in a flat or horizontal position prior to activity monitoring. In other embodiments, the method 800 may permit activity monitoring to occur when the person support apparatus 700 is in one or more other positions (such as positions in which the head zone 712 is elevated but the remainder of the person support apparatus 700 is flat). In still other embodiments, the method 800 may be configured to determine the position of the person support apparatus 700 and initialize the activity monitoring parameters and variables (block 812) based at least in part on the position of the person support apparatus 700. In such embodiments, block 810 may simply be used to determine whether a person is situated on the person support apparatus 700 (e.g., based on inputs from the force sensors 736, 738). If a person is not positioned on the person support apparatus 700, or if the person support apparatus 700 is not in a proper position for activity monitoring, the method 800 remains at block 810 until it times out, or the person support apparatus 700 is powered off, for example. If a person is positioned on the person support apparatus 700, or if the person support apparatus 700 is in a proper position for activity monitoring, the method 800 proceeds to block 812.

At block 812, the method 800 initializes parameters and variables that are used by the method 800 to determine the person's activity level based on inputs from sensors associated with the person support apparatus 700. More specifically, threshold values for determining when the person's activity constitutes a major or minor movement are determined or set (e.g., calculated or obtained from a lookup table) at block 812. The activity threshold values may be adjusted based on the person's weight (as determined, e.g., by the weigh scale 740 or based on manual input of the person's weight by a caregiver via a user interface), and/or the position of the person support apparatus 700. Alternatively or in addition, weighting and/or normalization factors used in the activity level calculations described below may be calculated or set at block 812. For example, sensor data may be weighted according to the person's body mass distribution on the person support apparatus 700 (e.g. if the person's weight is concentrated in the seat zone 714, sensor values obtained from the sensor(s) (e.g., pressure sensor 722) may be weighted more heavily than sensor values obtained from the sensors monitoring the other zones of the person support apparatus 700.

At block 814, the method 800 begins collecting data from the sensors used for activity monitoring. In the illustrative embodiment, the pressure sensors 720, 722, 724 are used for the activity monitoring. The data is collected at a predetermined sampling rate (e.g., about every 50 milliseconds). Calculations relating to the determination of activity level begin after a predetermined period of time or number of samples, to allow sufficient data to accumulate to make the calculations useful. For example, in the illustrative embodiment, processing of the sensor data begins after about 20 samples have been collected from each of the sensors 720, 722, 724, and the calculation of mean values is performed after about every 50 sets of data have been collected. Of course, the rates at which data is collected and at which values are calculated may vary according to the requirements of a particular design or implementation of the method 800.

At block 816, the method calculates the current activity level of the person positioned on the person support apparatus 700, based on the pressure values received from the sensors 720, 722, 724. The current activity level is determined as a function of the coefficient of variation (e.g., the ratio between the standard deviation and the mean) of the pressure values at each of the sensors 720, 722, 724. As described further in connection with FIG. 9, the coefficient of variation, e.g., $c_v = \sigma/\mu$, where $\sigma$=the standard deviation of the sampled set of pressure values and $\mu$=the mean value for the sampled set of pressure values, is calculated separately for each pressure zone 712, 714, 716. The coefficient of variation for each zone 712, 714, 716 is then modified by an adjustment that represents the percent of the time (e.g., the rate) or the number of times that the activity thresholds have been exceeded during the sampling period. While the coefficient of variation tends to eliminate variations due to the patient's weight, it may tend to exaggerate the activity level of a given movement (e.g., the same number of major and minor movements can lead to the same activity level). The adjustment is used to more easily distinguish minor movements from major movements. For example, taking into consideration the percentage of time that the coefficient of variation exceeds the threshold value, the activity level calculated based on minor movements should be lower while the activity level calculated based on major movements should remain higher. The person's overall activity level (over all zones of the patient support apparatus 700) is calculated as a scaled and weighted average of the individual coefficients of variation and adjustment values.

At block 818, the method 800 determines whether the person's instantaneous activity level (e.g., the coefficient of variation calculated at a given point in time) is greater than the activity threshold value used to detect minor movements. If, at block 818 the person's instantaneous activity level is determined not to be greater than the activity threshold for minor movement, then the method returns to block 814 without incrementing either the major or minor movement counters.

If the person's instantaneous activity level is determined to be greater than the activity threshold for minor movement, then the method proceeds to block 820. At block 820, the method 800 determines whether the person's instantaneous activity level is greater than the activity threshold value used to detect major movements. The minor and major activity level threshold values may be determined based on experimentation and may be modified by other factors, such as the person's weight, position on the person support apparatus 700, or the configuration of the person support apparatus 700, as discussed above. If, at block 820, the person's instantaneous activity level is determined to exceed the major movement threshold, then a major movement counter is incremented at block 822. If the person's instantaneous activity level is determined not to exceed the major movement threshold, then a minor movement counter is incremented at block 824. The major and minor movement counters are positive integers and are incremented by 1 each time a major or minor movement, as the case may be, is detected. Data relating to the detection of major and minor movements is collected for a period of time, time period1, which is predetermined as discussed above. At block 826, if the time period1 has not elapsed, then the method 800 returns to block 814 and continues monitoring the person's activity level at the person support apparatus 700. When the time period1 has expired, the method 800 proceeds to block 828, where a mobility score can be calculated for the person, based on the frequency of the major and minor movements detected by the method 800 using data collected by the sensors 720, 722, 724.

At block 828, the method 800 analyzes the major and minor movement counter values and determines the percentage of time that major and minor movement occurred during the sample period. These percentages can be correlated to a mobility score (such as a Braden score), as shown in TABLE 1 below.

TABLE 1

| Minor Movement | <1% | 1%-30% | 30%-50% | 50%-100% |
|---|---|---|---|---|
| | | AND | | |
| Major Movement Score | <1% 1 | 1%-10% 2 | 10%-20% 3 | 20%-100% 4 |

So, for example, if, based on the counter value for minor movements, minor movements occurred less than 1% of the time during the sample period, and, based on the counter value for major movements, major movements occurred less than 1% of the time during the sample period, the person may be assigned a mobility score of 1. In the illustrated example, a higher percentage of major and minor movements generally results in a higher mobility score, although this need not be the case. In some examples, a combination of a lower percentage of major movements and higher percentage of minor movements may result in a higher mobility score, or a combination of a lower percentage of minor movements and a higher percentage of major movements may result in a higher mobility score. In some embodiments, a higher mobility score may indicate greater mobility; while in other embodiments, a higher mobility score may indicate less mobility. The mobility scoring mechanisms can be adapted to the requirements of a particular design or implementation of the method 800.

Figure 9:
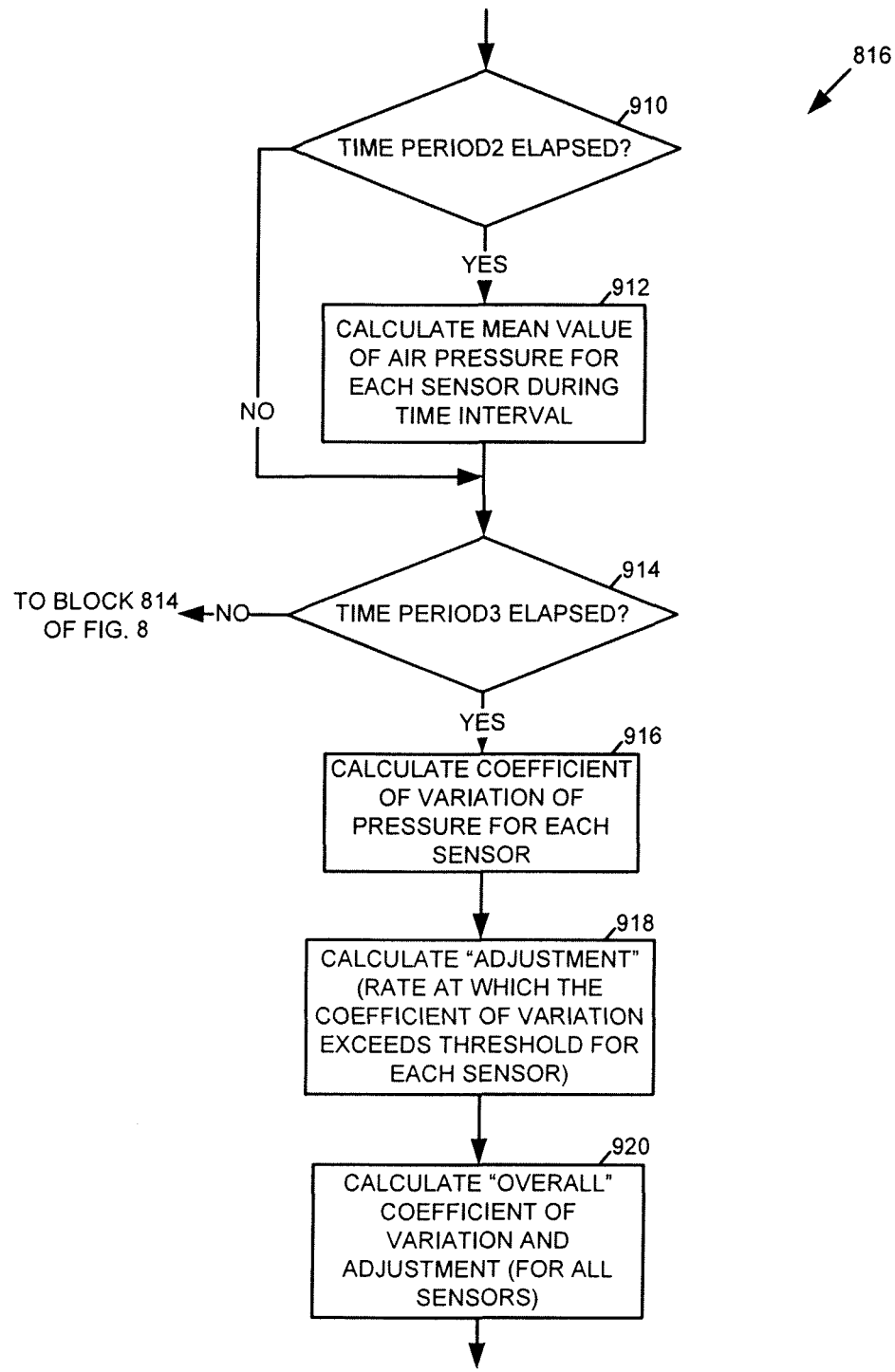
FIG. 9 is a simplified flow diagram of at least one embodiment of a method for calculating an activity level.

Referring now to FIG. 9, the method 816 for calculating the person's instantaneous activity level is illustrated in greater detail. As mentioned above, the method 800 calculates the mean pressure value for each sensor 720, 722, 724 at predetermined time intervals during the monitoring period. This predetermined time interval is referred to as time period2 in FIG. 9. If the time period2 has elapsed, the method 816 proceeds to calculate the mean value of the air pressure values collected by each of the sensors 720, 722, 724 during the monitoring period, at block 912. If the time period2 has not elapsed, the method 816 proceeds to block 914 without calculating the mean value. At block 914, the method 816 determines whether the time interval for calculating the coefficient of variation, time period3, has elapsed. If the time period3 has not elapsed, the method 816 returns to block 814 of FIG. 8 and continues collecting pressure data from the sensors 720, 722, 724. In some embodiments, the time period3 for calculating coefficient of variation is in the range of about every 1 second, while the time period2 for calculating the mean is in the range of about every 5 seconds.

At block 916, the coefficient of variation is calculated (as the ratio of standard deviation to mean), for each of the sensors 720, 722, 724. At block 918, the adjustment (e.g., the rate at which the coefficient of variation exceeds the threshold) is calculated based on the history of the coefficient of variation data over the time interval. At block 920, the individual activity level calculations (e.g., coefficient of variation and adjustment value for each sensor 720, 722, 724, are combined to generate an overall activity level for the person support apparatus 700 (e.g., considering all of the monitored zones 712, 714, 716).

In some embodiments, the overall activity level (or "activity score") may be continuously calculated, e.g., each time the coefficient of variation is calculated. For example, in some embodiments, the equation for calculating the overall activity score is equal to the sum of: the coefficient of variation multiplied by a normalization factor and multiplied by a weighting factor. In the illustrated embodiment, this equates to: [(coefficient of variation for head zone 712)*(normalization factor for head zone 712)*(weighting factor for head zone 712)]+[(coefficient of variation for seat zone 714)*(normalization factor for seat zone 714)*(weighting factor for seat zone 714)]+[(coefficient of variation for foot zone 716)*(normalization factor for seat zone 716)*(weighting factor for seat zone 716)]. As discussed above, the weighting factor applied to each of the zones 712, 714, 716 is a scalar that can be used to allow one or more of the zones to have greater or lesser significance in the activity level calculations. The normalization factors are simply scalars that are used to normalize the results of the calculations to some predefined range. For example, in some embodiments, the normalization factors are used to normalize the results to a range between 0 and 100 (or 0% and 100%), so that an activity level near zero represents low activity during the monitoring period and an activity level near 100 represents high activity during the monitoring period. Of course, any suitable normalizing technique may be used, as may be required or desirable according to a specific design or implementation of the method 800 or the person support apparatus 700.

In other embodiments, the overall activity level may be calculated based on the sheer number of times the coefficient of variation exceeds the threshold values (e.g., goes above the upper threshold value or below the lower threshold value) during the monitoring period; in other words, based on the major and/or minor movement counter values for each of the zones 712, 714, 716. This value is referred to as the "NUMRISE" below and in FIG. 10. For example, in the illustrative embodiments, the equation for calculating the overall activity score is equal to the sum of: [(NUMRISE for head zone 712)*(weighting factor for head zone 712)]+[(NUMRISE for seat zone 714)*(weighting factor for seat zone 714)]+[(NUMRISE for foot zone 716)*(weighting factor for foot zone 716)].

Figure 10:
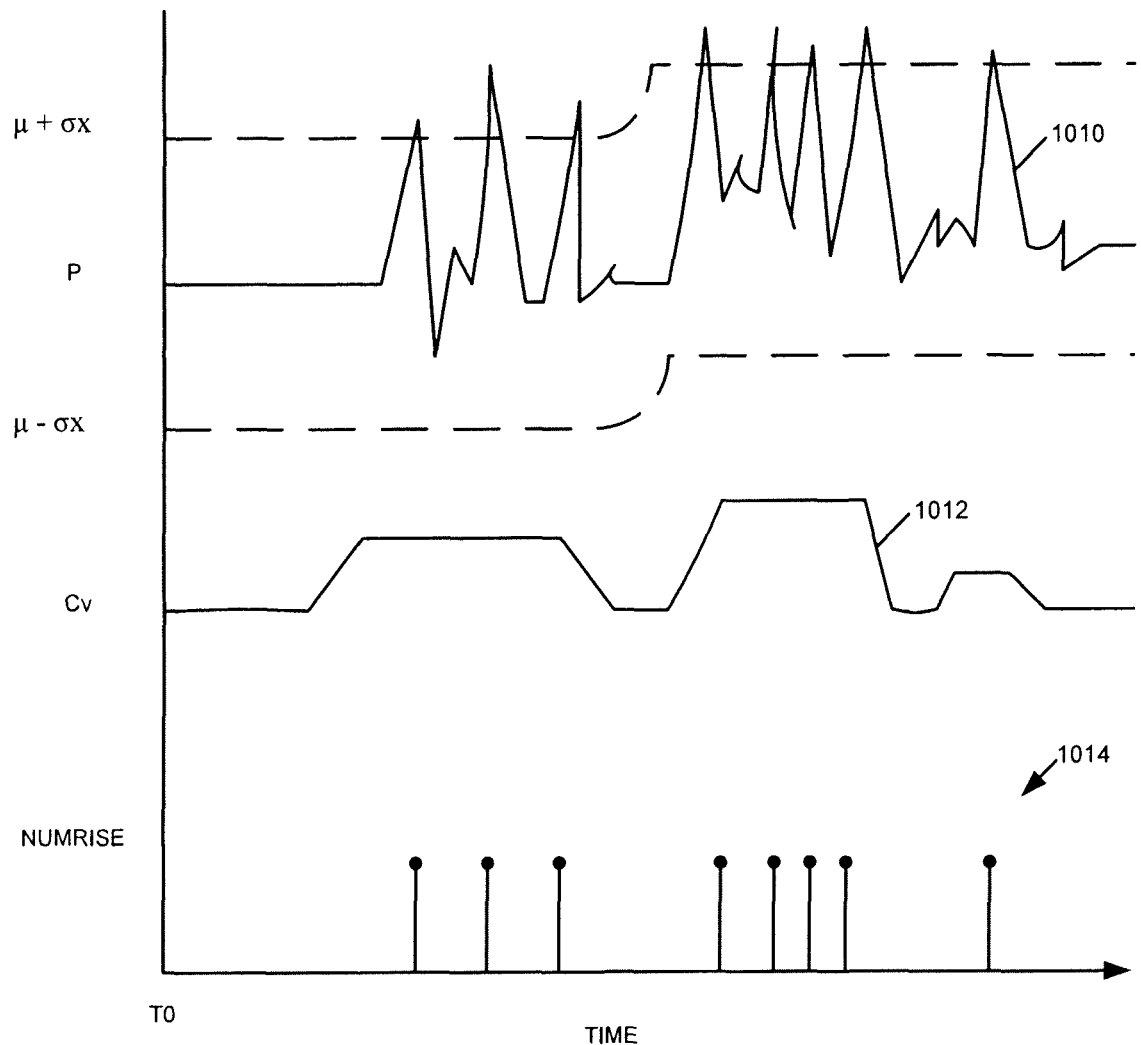
FIG. 10 is a simplified plot illustrating various parameters that may be used in determining activity and/or mobility level of a person on a person support apparatus.

Referring now to FIG. 10, a simplified plot of pressure readings 1010 from one of the sensors 720, 722, 724 ("P") is shown, along with the related coefficient of variation ("Cv") 1012 and the NUMRISE 1014. In the illustrated example, the NUMRISE counter is incremented each time the rising pressure curve exceeds the upper threshold ($\mu+\sigma x$) or goes below the lower threshold ($\mu-\sigma x$), where "x" represents a scalar that can be used to adjust the sensitivity of the activity monitoring routine 732. For instance, a higher value of x will decrease the sensitivity of the activity monitoring routine 732 (so that pressure variations need to be greater in degree in order to be considered movements exceeding the threshold), while a lower value of x will increase the sensitivity of the activity monitoring routine 732 (so that pressure variations that are smaller in degree may be considered movements exceeding the threshold). The sensitivity factor may be adjusted based on one or more characteristics of the person support apparatus 700 (e.g., characteristics of the person support surface 710, the current operating mode of the person support surface 710, and/or others), or one or more characteristics of the person (e.g., the person's weight, health condition, existence of pressure ulcers, and/or other factors), for example.

There are many advantages of the present disclosure arising from the various features described herein. It will be noted that alternative embodiments of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A person support system, comprising:
a person support apparatus configured to support a person in one or more positions,
at least one sensor coupled to the person support apparatus, the at least one sensor being responsive to changes in the position of a person relative to the person support apparatus while the person is supported by the person support apparatus, and a control system operably coupled to the at least one sensor and the person support apparatus, the control system being configured to:
receive a plurality of outputs from the at least one sensor over a period of time,
make an assessment relating to the person's activity and mobility, wherein the assessment relating to the person's mobility is indicated by changes in position of the person's body or an extremity thereof, relative to the person support apparatus, the changes in position being greater in degree than movement that indicates physiological activity of the person and less in degree than changes in position that indicate a major change in the person's position, and the assessment relating to the person's activity is indicated by changes in the person's position that are greater in degree than the changes in position relating to mobility,
determine a person type of the person being supported by the person support apparatus based on the activity and mobility assessment, the person type indicative of a degree of risk of breakdown of bodily tissue,
enable, disable, or configure an electronically-controllable feature of the person support apparatus based on the person type;
wherein the assessment relating to the person's overall activity level is calculated as a sealed and weighted average of individual coefficients of variation of pressure values at each of the at least one sensor and adjustment values that represent a percent of the time or a number of times that activity thresholds have been exceeded during the sampling period;
wherein the assessment relating to the person's mobility is derived from the outputs by: receiving a plurality of first outputs from the at least one sensor, the plurality of first outputs indicative of small-scale changes in the person's position relative to the person support apparatus over time while the person is supported by the person support apparatus; calculating a mobility score as a function of changes in magnitude of the first outputs over a time interval and a frequency of the changes in magnitude during the time interval; and comparing the mobility score to a threshold value.

2. The person support system of claim 1, wherein the person support apparatus is one of a mattress, cushion, bed, stretcher, chair, and table.

3. The person support system of claim 1, wherein the at least one sensor is at least one of a load cell, inclinometer, accelerometer, pressure sensor, force sensor, and optical sensor.

4. The person support system of claim 1, wherein the control system is included in an on-board control system of the person support apparatus.

5. The person support system of claim 1, wherein the control system sets a time period during which the outputs of the at least one sensor are monitored and performs a mathematical calculation using data represented by the outputs received during the time period to determine an activity and/or mobility score.

6. The person support system of claim 5, wherein the control system compares the calculated activity to a threshold activity.

7. The person support system of claim 1, wherein the control system is configured to display an indication of the person's activity and/or mobility at a display that is coupled to the person support apparatus.

8. The person support system of claim 1, wherein the control system communicates an indication of the person's activity and/or mobility to a remote device.

9. The person support system of claim 1, wherein the control system enables an electronically controllable feature of the person support apparatus if the person type is a first person type and disables an electronically controllable feature of the person support apparatus if the person type is a second person type different than the first person type.

10. The person support system of claim 1, wherein the control system selects a person type from a plurality of person types based on the person's activity and/or mobility assessment.

11. The person support system of claim 1, wherein the control system configures a user control based on the person type.

12. The person support system of claim 1, wherein the control system uses a first plurality of the plurality of the outputs to calibrate the activity and/or mobility assessment.

13. The person support system of claim 1, wherein the control system permits a user to override the enabling, disabling, or configuring of an electronically-controllable feature of the person support apparatus based on the person type.

14. The person support system of claim 1, wherein the enabling, disabling, or configuring of an electronically-controllable feature of the person support apparatus based on the person type comprises enabling a user to enable, disable, or configure an electronically-controllable feature of the person support apparatus based on the person type.

15. The person support system of claim 1 wherein the control system is configured to define a person-specific magnitude range of the first outputs based on a person-specific factor comprising one or more of body weight and body type, and calculate the mobility score based on magnitude changes that are in the person-specific magnitude range.

16. The person support system of claim 1, wherein the control system is configured to receive a plurality of second outputs from the at least one sensor, the plurality of second outputs are indicative of large-scale changes in the person's position relative to the person support apparatus over time while the person is supported by the person support apparatus, the control system is to calculate a combined activity and mobility score, and the control system is to determine the risk assessment based on the combined activity and mobility score.

17. The person support system of claim 16, wherein the control system is configured to distinguish between the first outputs and the second outputs using a mathematical technique.

18. The person support system of claim 16, wherein the control system is configured to monitor the first outputs and the second outputs over different time intervals.

19. A control system for a person support apparatus, the control system comprising:
   at least one sensor coupled to the person support apparatus, the at least one sensor being responsive to changes in the position of a person while the person is supported by the person support apparatus, and
   a processor operably coupled to the at least one sensor and the person support apparatus, the processor being configured to:
      receive a plurality of first outputs from the at least one sensor, the plurality of first outputs being indicative of the person's position relative to the person support apparatus while the person is supported by the person support apparatus,
      make an assessment relating to the person's mobility wherein the assessment of the person's mobility is based on changes in position of the person's body or an extremity thereof, the changes in position being greater in degree than movement that indicates physiological activity of the person and less in degree than changes in position that indicate a major change in the person's position,
      determine a person type of the person being supported by the person support apparatus based on the mobility assessment, the person type indicative of a degree of risk of breakdown of bodily tissue,
      enable, disable, or configure an electronically-controllable feature of the person support apparatus based on the person type;
      wherein the assessment relating to the person's overall activity level is calculated as a scaled and weighted average of individual coefficients of variation of pressure values at each of the at least one sensor and adjustment values that represent a percent of the time or a number of times that activity thresholds have been exceeded during the sampling period;
      wherein the assessment relating to the person's mobility is derived from the outputs by: receiving a plurality of first outputs from the at least one sensor, the plurality of first outputs indicative of small-scale changes in the person's position relative to the person support apparatus over time while the person is supported by the person support apparatus;
      calculating a mobility score as a function of changes in magnitude of the first outputs over a time interval and a frequency of the changes in magnitude during the time interval; and comparing the mobility score to a threshold value.

20. The control system of claim 19, wherein the processor is configured to receive a plurality of second outputs from the at least one sensor, wherein the plurality of second outputs are indicative of the person's position relative to the person support apparatus, and make an assessment relating to the person's degree of physical activity, based on the second outputs, where the assessment of the person's degree of physical activity is based on changes in the position of the person's body or an extremity thereof, which are greater than changes in position that indicate the person's mobility.

21. The control system of claim 20, wherein the assessment of the person's degree of physical activity is indicative of the person's ability to ingress or egress the person support apparatus without assistance from another person.

22. The control system of claim 20, wherein the processor determines the person type based on the mobility assessment and the activity assessment.

23. The control system of claim 19, wherein the person support apparatus comprises an air bladder and the processor enables, disables, or configures an air pressure feature of the person support apparatus based on the person type.

24. The control system of claim 19, wherein the person support apparatus comprises a low airloss feature and the processor enables, disables, or configures the low airloss feature based on the person type.

25. The control system of claim 19, wherein the person support apparatus comprises an articulating deck and the processor enables, disables, or configures a feature of the articulating deck based on the person type.

26. The control system of claim 19, wherein the person support apparatus comprises a plurality of therapy features and the processor enables, disables, or configures a therapy feature of the person support apparatus based on the person type.

* * * * *